United States Patent [19]

Miki et al.

[11] Patent Number: 4,994,571

[45] Date of Patent: Feb. 19, 1991

[54] PROCESS OF PRODUCING SULFONYLUREA DERIVATIVES

[75] Inventors: Hideki Miki, Tokyo; Yasuo Ishida, Suita, both of Japan

[73] Assignee: Takeda Chemical Industries, Ltd., Osaka, Japan

[21] Appl. No.: 237,231

[22] Filed: Aug. 26, 1988

[30] Foreign Application Priority Data

Aug. 31, 1987 [JP] Japan .................. 62-218963

[51] Int. Cl.$^5$ ............... C07D 401/14; C07D 403/14; C07D 413/14; C07D 417/14
[52] U.S. Cl. ...................... 544/331; 544/212; 544/236; 544/252; 544/281
[58] Field of Search ............... 544/212, 236, 281, 331, 544/252

[56] References Cited

U.S. PATENT DOCUMENTS

| | | | |
|---|---|---|---|
| 4,443,243 | 4/1984 | Fory et al. | 544/211 |
| 4,656,273 | 4/1987 | Topfl | 544/211 |
| 4,681,620 | 7/1987 | Bohner et al. | 71/93 |
| 4,921,527 | 5/1990 | Tseng | 544/236 |

FOREIGN PATENT DOCUMENTS

0203679 12/1986 European Pat. Off. .
0224842 6/1987 European Pat. Off. .
0238070 9/1987 European Pat. Off. .

*Primary Examiner*—Mukund J. Shah
*Assistant Examiner*—E. Bernhardt
*Attorney, Agent, or Firm*—Wenderoth, Lind & Ponack

[57] ABSTRACT

This invention relates to a process for producing a compound of the formula (I) as shown below.

$$Q-SO_2NH_2 \qquad Y_1-\overset{O}{\underset{\|}{C}}-OY_2$$

(IV) \qquad (III)

$$\downarrow \text{base}$$

$$\left( Q-SO_2NH-\overset{O}{\underset{\|}{C}}-OY_2 \right)$$

$$H_2N\!-\!\!\left\langle\!\!\begin{array}{c} N=\!\!\left\langle\!\!\begin{array}{c} R_1 \\ \\ Z \\ \\ R_2 \end{array}\right. \end{array}\right. \quad (II)$$

$$\downarrow$$

$$Q-SO_2NH-\overset{O}{\underset{\|}{C}}-NH\!-\!\!\left\langle\!\!\begin{array}{c} N=\!\!\left\langle\!\!\begin{array}{c} R_1 \\ \\ Z \\ \\ R_2 \end{array}\right. \end{array}\right. \quad (I)$$

wherein Q is a condensed heterocyclic group having a nitrogen atom in the bridgehead position which may optionally be substituted, $R_1$ and $R_2$ each are an alkyl group, an alkoxy group or halogen and Z is CH or N, or a salt thereof.

The compound (I) or a salt thereof is novel and of value as agricultural chemicals.

According to the process of this invention the compound (I) or a salt thereof can be produced in good yield and high purity.

3 Claims, No Drawings

PROCESS OF PRODUCING SULFONYLUREA DERIVATIVES

This invention relates to a process of producing novel sulfonylurea derivatives which exert herbicidal activity.

More particularly, this invention relates to a process for producing a compound of the formula (I)

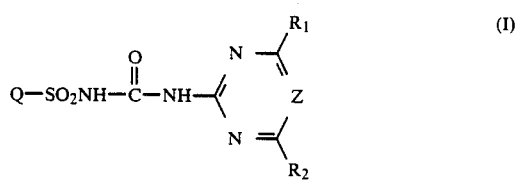

wherein Q is a condensed heterocyclic group having a nitrogen atom in the bridgehead position which may optionally be substituted, $R_1$ and $R_2$ each are an alkyl group, an alkoxy group or halogen and Z is CH or N, or a salt thereof which comprises the 1st step of reacting a compound of the formula (IV)

$$Q-SO_2NH_2 \quad (IV)$$

wherein the symbols are as defined above, with a compound of the formula (III)

wherein $Y_1$ is halogen or $-OY_2$, and $Y_2$ is an alkyl group or phenyl, in the presence of a base, and the 2nd step of allowing a compound of the formula (II)

and an acid to act on the reaction product in the reaction mixture of the 1st step under anhydrous conditions.

The sulfonylurea derivatives obtained by the process of the present invention are novel and are of value as agricultural chemicals, such as herbicides.

Hitherto, according to the prior art, a sulfonylurea derivative which is different from the end product of the present invention is produced by a two-step process in which a sulfonamide is reacted with a chloroformate or a carbonic diester to obtain a sulfonylcarbamate compound, and after isolating and purifing it, the resulting compound is further reacted with an amine compound to obtain a sulfonyl urea compound. For example, Japanese Published Unexamined Patent Application No. 78980/1985 describes a two-step process as shown below.

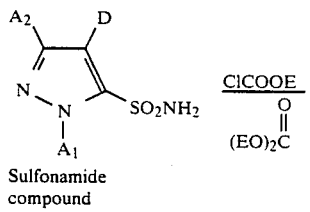
Sulfonamide compound

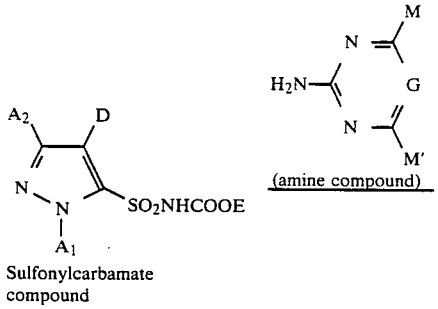
Sulfonylcarbamate compound

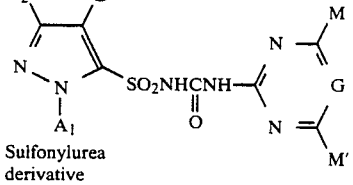
Sulfonylurea derivative wherein $A_1$ is hydrogen or lower alkyl; $A_2$ is hydrogen or lower alkyl; D is hydrogen, lower alkyl or $-COOR$ (R is hydrogen or lower alkyl); E is alkyl or phenyl; G is nitrogen or $=$ $$\overset{|}{C}-R' \quad (R' \text{ is hydrogen});$$

M and M' each are hydrogen, lower alkyl, lower alkoxy and so on. However, the present inventors have tried to produce the compound (I) through the process of the known prior art, but have found that this process is disadvantageous in that (1) it comprises a two-step process involving complicated procedures, (2) it provides the final compound only in low yield and low purity, and (3) the sulfonylcarbamate compound obtained by the 1st step is unstable to moisture as well as heat and is difficult to handle. Thus this known process is unsatisfactory as industrial method.

In the process of this invention, the compound of formula (IV) is reacted with a compound of formula (III) to obtain the sulfonylcarbamate compound of formula

wherein the symbols are as defined above, (the 1st step) and the resulting compound (V) is reacted with a compound of formula (II) without isolation from the reaction mixture to obtain the compound (I) in high purity and high yield (the 2nd step).

The compounds produced by the process of the invention are novel and have not been described in prior publications.

In the above formulas (I), (IV) and (V), Q is a condensed heterocyclic group having a nitrogen atom in the bridgehead position, which may optionally be substituted. The condensed heterocyclic group having a nitrogen atom in the bridgehead means a condensed heterocyclic group having a nitrogen atom at either or one of its first and second bridgeheads. The condensed heterocyclic group having a nitrogen atom in the bridgehead, as represented by Q, is a group derived from a heterocyclic ring, which is represented by the general formula

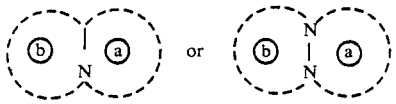

wherein ring a and ring b each are a nitrogen-containing heterocyclic ring which may optionally be substituted, by removing one hydrogen atom attached to one of the ring-constituent carbon atoms other than the bridgehead atoms. The condensed heterocyclic group is represented by the general formula

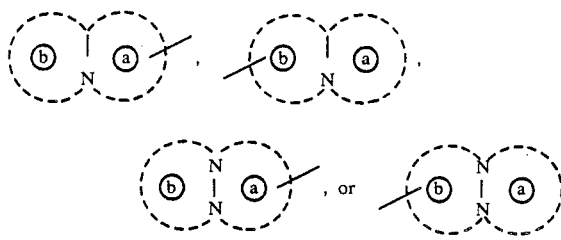

wherein — means a chemical bond; other symbols are as defined above.

The nitrogen-containing heterocyclic ring represented by ring ⓐ or ring ⓑ is a 4- to 8-membered, preferably 5- or 6-membered heterocyclic ring containing 1 to 4 nitrogen atoms and optionally containing 1 to 3 oxygen atoms and/or 1 to 3 sulfur atoms which may be mono- or di-oxidized, which may further be fused to a 5- or 6-membered alicyclic ring (for example, cyclopentane or cyclohexane), an aromatic ring (for example, benzene or naphthalene) or a heterocyclic ring (preferably a 5- or 6-membered heterocyclic ring).

Among the above groups, the groups having the general formula

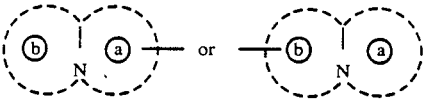

are preferable.

In the above formulas, ring ⓐ is a 5-membered heterocyclic ring containing 1 to 3 nitrogen atoms and ring ⓑ is preferably a 6-members heterocyclic ring containing 1 to 2 nitrogen atoms or a 5-membered heterocyclic ring containing 1 or 2 nitrogen atoms and 1 sulfur atom which may be mono- or dioxidized.

The rings ⓐ and ⓑ may each be substituted by the same or different 1 to 3 substituents of $B_1$, $B_2$ and $B_3$ which are defined hereinafter.

Specifically the group of the general formula

is represented by the general formula

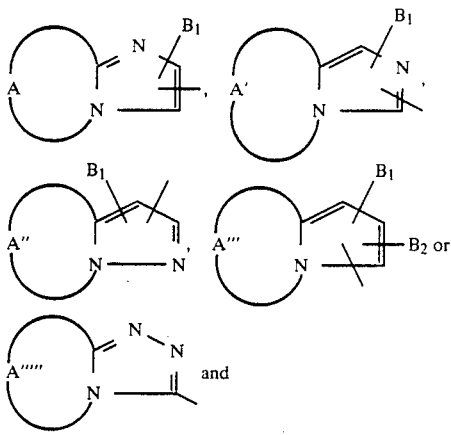

the group of general formula

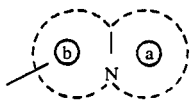

is represented by the general formula

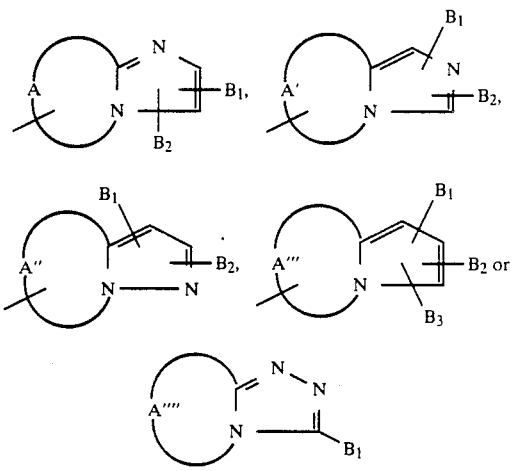

wherein A is a group forming a condensed ring at the [1,2] position of the imidazole ring; A' is a group forming a condensed ring at the [1,5] position of the imidazole ring; A'' is a group forming a condensed ring at the [1,5] position of the pyrazole ring; A''' is a group forming a condensed ring at the [1,2] position of the pyrrole ring; A'''' is a group forming a condensed ring at the [3,4] position of the triazole ring; and $B_1$, $B_2$ and $B_3$ each are hydrogen, hydroxy, amino, cyano, sulfamoyl, sulfamoyloxy, mercapto, nitro, halogen or an organic residue. The carbon and nitrogen atoms constituting the ring of group A, A', A'', A''' or A'''' may have 1 to 3 of the same or different substituents such as hydroxy, amino, cyano, sulfamoyl, sulfamoyloxy, mercapto, nitro, halogen, an organic residue or sulfo. The adjoining carbon and nitrogen atoms or the adjoining carbon and carbon atoms which constitute a ring atom may form a further condensed ring (5- or 6-membered condensed ring). Moreover, the ring-constituting sulfur atom may be mono- or dioxidized.

The organic residue $B_1$, $B_2$ or $B_3$ has the same meaning as that of substituent on the condensed heterocyclic ring which is defined hereinafter.

The group A, A', A", A''' or A'''' contains 1 to 4, preferably 3 or 4, carbon atoms as ring-constituent atoms and may further contain 1 to 3 nitrogen, oxygen or/and sulfur atoms which may be mono- or dioxidized.

The condensed ring of

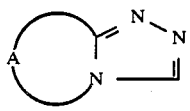

which is the skeleton of the group of the general formula

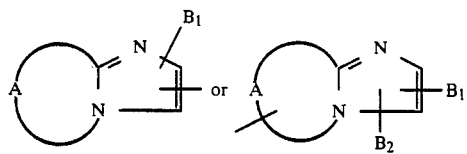

includes, among others,

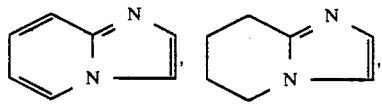
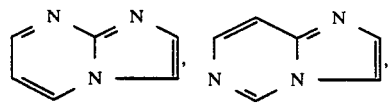
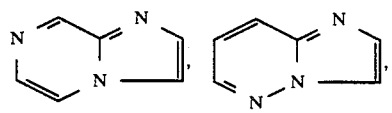
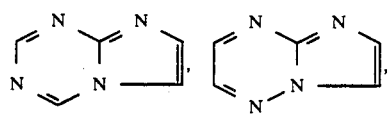
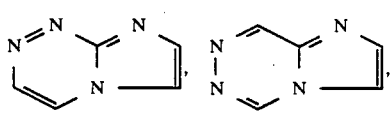
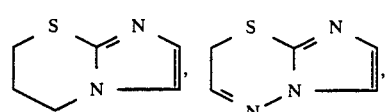

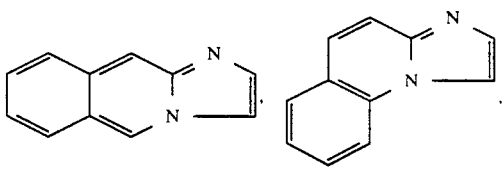
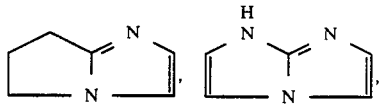
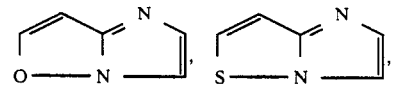
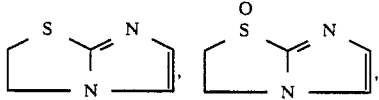
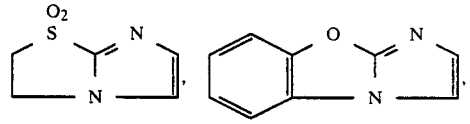
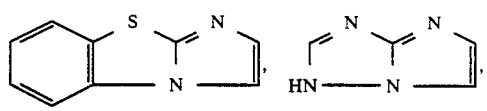
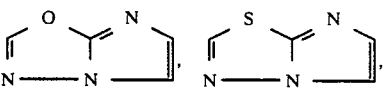
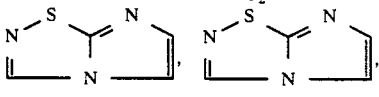
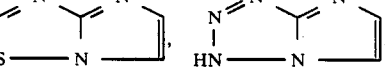
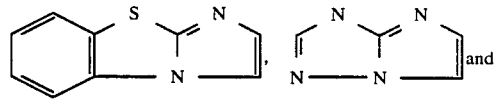
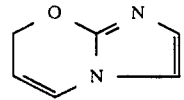

The condensed ring of the general formula

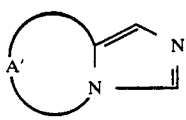

which is the skeleton of the group of the general formula

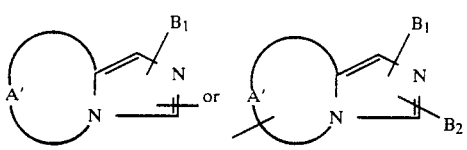

includes, among others,

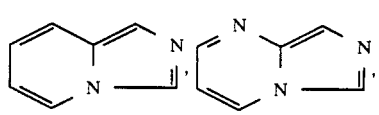

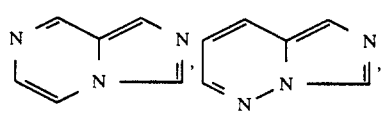

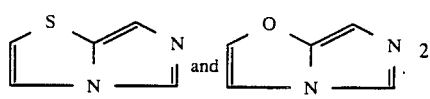

The condensed ring of the general formula

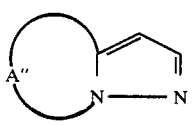

which is the skeleton of the group of the general formula

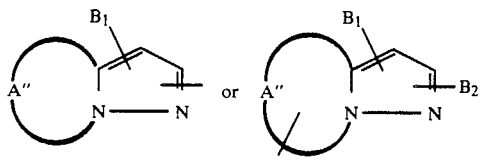

includes, among others,

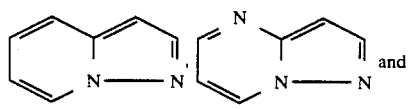

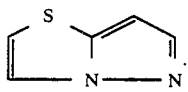

The condensed ring of the general formula

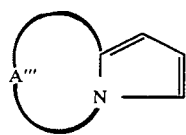

which is the skeleton of the group of the general formula

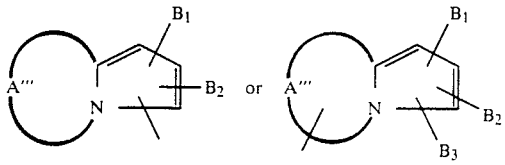

includes, among others,

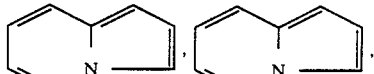

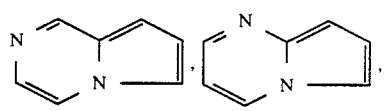

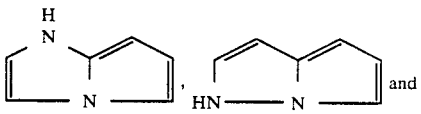

The condensed ring of the general formula

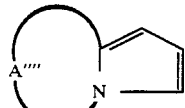

which is the skeleton of the group of the formula

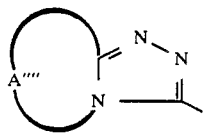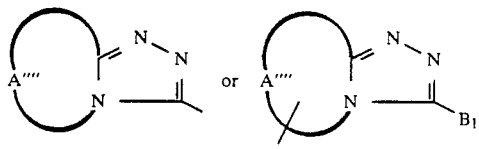

includes, among others,

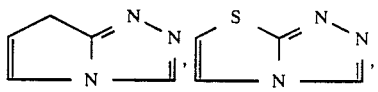

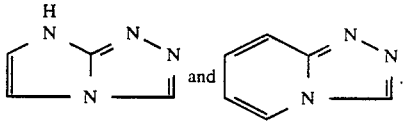

Among the above-mentioned condensed rings, preferably examples are imidazo[1,2-a]pyridine ( 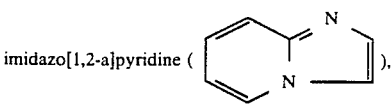 ), imidazo[2,1-b]thiazole ( 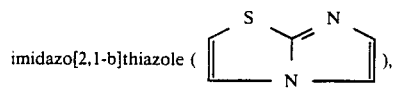 ), imidazo[1,2-a]pyrimidine ( 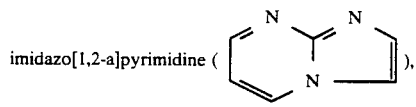 ), imidazo[1,2-b]pyridazine ( 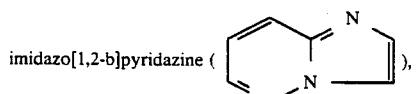 ), imidazo[1,2-c]pyrimidine ( 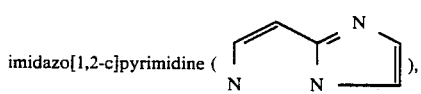 ), imidazo[1,2-a]imidazole ( 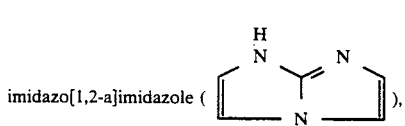 ), imidazo[2,1-b](1,3,4)thiadiazole ( 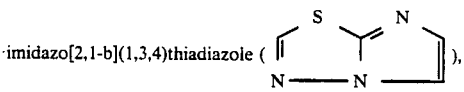 ), 2,3-dihydroimidazo[2,1-b]thiazole
(or its monoxide or dioxide)
(n is 0, 1 or 2) ( 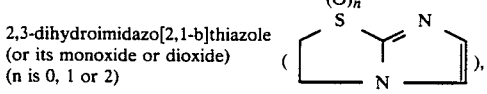 ), pyrazolo[1,5-a]pyramidine ( 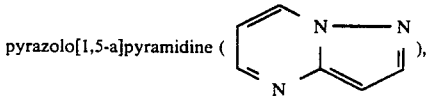 ), pyrazolo[5,1-b]thiazole ( 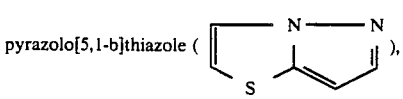 ), pyrazolo[1,5-a]pyridine ( 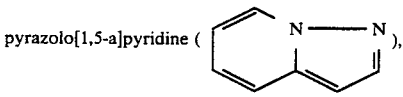 ), pyrrolo[1,2-a]pyridine ( 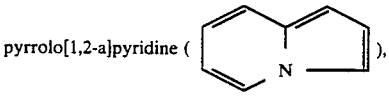 ), imidazo[1,5-a]pyridine ( 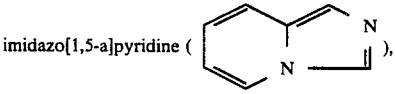 ), imidazo[1,2-b](1,2,4)triazole ( 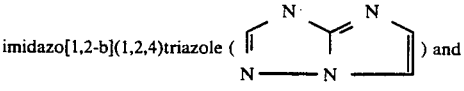 ) and (1,2,4)triazolo[3,4-b]thiazole (  ).

More preferred ones are imidazo[1,2-a]pyridine, imidazo[2,1-b]thiazole and imidazo[1,2-b]pyridazine.

The condensed heterocyclic group containing a nitrogen atom in the bridgehead position, represented by Q, is a group derived from the above-mentioned condensed heterocyclic ring by removal of one hydrogen atom attached to one of its constituent atoms other than the bridgehead atoms. For example, the condensed heterocyclic group corresponding to imidazo[1,2-a]pyridine, which is one of the above condensed heterocyclic ring, may be represented by the formula

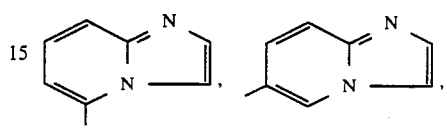

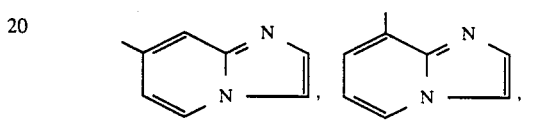

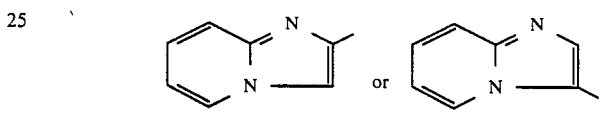

Among the groups mentioned hereinbefore, groups of the following general formula are preferred.

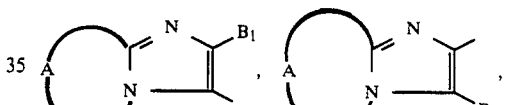

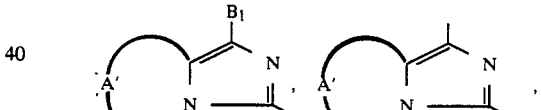

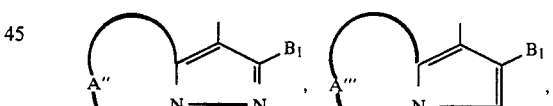

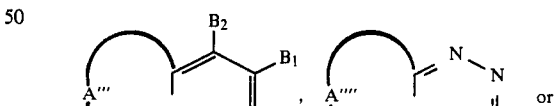

The group A preferably contains, as ring-constituent atoms, 4 carbon atoms, 2 to 3 carbon atoms and one nitrogen atom, 2 carbon atoms and one sulfur atom which may be mono- or dioxidized, one carbon atom, one sulfur atom and one nitrogen atom, or one carbon atom and 2 nitrogen atoms.

The group A' and A''' each contains preferably 4 carbon atoms as ring-constituent atoms.

The group A'' preferably contains 4 carbon atoms, 3 carbon atoms and one nitrogen atom, or two carbon atoms and one sulfur atom as ring-constituent atoms.

The group A'''' preferably contains 2 carbon atoms and one sulfur atom, as ring-constituent atoms.

The condensed heterocyclic group having a nitrogen atom in the bridgehead may be substituted by 1 to 3 of the same or different substituents, such as hydroxy, amino, cyano, sulfamoyl, sulfamoyloxy, mercapto, nitro, halogen, an organic residue or sulfo.

Preferred are cyano, sulfamoyl, sulfamoyloxy, nitro, halogen and organic residues. More preferable substituents are cyano, halogen and an organic residue.

Examples of the halogen mentioned above include fluorine, chlorine, bromine and iodine. Examples of the organic residue, mentioned above include, among others, a hydrocarbon group, a heterocyclic group, an acyl group, a group of the formula —T—$Q_0$ [where $Q_0$ is a hydrocarbon group, a heterocyclic group or an acyl group; T is O,

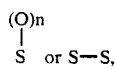

wherein n is equal to 0, 1 or 2], groups of the formula

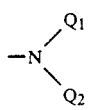

[where $Q_1$ is hydrogen, a hydrocarbon group or an acyl group; $Q_2$ is a hydrocarbon group or an acyl group], a group of the formula

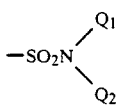

[where $Q_1$ and $Q_2$ are respectively as defined above], carbamoyl, carbamoyloxy, ureido, thiocarbamoyl, carboxyl, and a group of the formula —O—$SO_2$—$Q_2$ [where $Q_2$ is as defined above].

The hydrocarbon group, heterocyclic group and acyl group, mentioned as examples of said organic residues, the hydrocarbon group, heterocyclic group and acyl group represented by $Q_0$, and the hydrocarbon group and acyl group represented by $Q_1$ or $Q_2$ are described in detail hereinafter.

The aforesaid carbamoyl, carbamoyloxy, ureido or thiocarbamoyl group may be substituted by one or two of the same or different hydrocarbon groups, heterocyclic group and/or acyl groups which are described in detail hereinafter.

The heterocyclic group as an example of said organic residue and the heterocyclic group represented by $Q_0$ may be substituted by 1 to 3 of the hydrocarbon groups, acyl group and halogen which are described in detail hereinafter.

Examples of the hydrocarbon group include a straight-chain, branched or cyclic aliphalic groups which may contain a double bond or a triple bond, an aryl group or an aralkyl group and more concretely, an alkyl group, an alkenyl group, an alkynyl group, an aryl group or an aralkyl group.

The alkyl group is preferably a straight-chain, branched or cyclic alkyl group containing 1 to 6 carbon atoms, such as methyl, ethyl, n-propyl, isopropyl, n-butyl, isobutyl, sec-butyl, tert-butyl, n-pentyl, sec-pentyl, isopentyl, neopentyl, cyclopentyl, n-hexyl, isohexyl or cyclohexyl. The alkenyl group is preferably a straight-chain, branched or cyclic alkenyl group containing 3 to 6 carbon atoms, such as allyl, isopropenyl, 1-butenyl, 2-pentenyl or 2-hexenyl. The alkynyl group is preferably an alkynyl group containing 3 to 6 carbon atoms, such as propargyl, 2-butynyl, 3-butynyl, 3-pentynyl or 3-hexynyl. The aryl group is preferably an aryl group containing 6 to 14 carbon atoms, such as phenyl, naphthyl, biphenylyl or anthryl. The aralkyl group is preferably an aralkyl group containing 7 to 19 carbon atoms, such as benzyl, phenethyl, phenylpropyl, biphenylylmethyl, benzhydryl or trityl. The heterocyclic group is exemplified by a 5- or 6-membered heterocyclic group containing 1 to 4 hetero atoms, such as nitrogen which may be oxidized, oxygen and sulfur which may be mono- or dioxidized or a condensed cyclic group thereof preferably a condensed cyclic group formed between said 5- or 6-membered heterocyclic group and a 5- or 6-membered cyclic group which may contain 1 to 4 hetero atoms, such as nitrogen which may be oxidized, oxygen and sulfur which may be mono- or dioxidized. Specific examples of the heterocyclic group include 2- or 3-pyrrolyl, 3-, 4- or 5-pyrazolyl, 2-, 4- or 5-imidazolyl, 1,2,3-triazol-4-yl, 1,2,4-triazol-3-yl, 1H- or 2H-tetrazol-5-yl, 2- or 3-furyl, 2- or 3-thienyl, 2- or 3-thienyl-1,1-dioxido, 2-, 4- or 5-oxazolyl, 3-, 4- or 5-isoxazolyl, 1,2,3-oxadiazol-4 or 5-yl, 1,2,4-oxadiazol-3 or 5-yl, 1,2,5-oxadiazol-3 or 4-yl, 1,3,4-oxadiazol-2 or 5-yl, 2-, 4- or 5-thiazolyl, 3-, 4- or 5-isothiazolyl, 1,2,3-thiadiazol-4 or 5-yl, 1,2,4-thiadiazol-3- or 5-yl, 1,2,5-thiadiazol-3- or 4-yl, 1,3,4-thiadiazol-2 or 5-yl, 2- or 3-pyrrolidinyl, 2-, 3- or 4-pyridyl, 2-, 3- or 4-pyridyl-N-oxido, 3- or 4-pyridazinyl, 3- or 4-pyridazinyl-N-oxido, 2-, 4- or 5-pyrimidinyl, 2-, 4- or 5-pyrimidinyl-N-oxido, pyrazinyl, 2-, 3- or 4-piperidinyl, piperazinyl, 3H-indol-2 or 3-yl, 2-, 3- or 4-pyranyl, 2-, 3- or 4-thiopyranyl, 2-, 3- or 4-thiopyranyl-1,1-dioxido, benzopyranyl, 3-, 4-, 5-, 6-, 7- or 8-quinolyl, pyrido[2,3-d]pyrimidinyl (e.g. pyrido[2,3-d]pyrimidin-2-yl), 1,5-, 1,6-, 1,7-, 1,8-, 2,6- or 2,7-naphthyridinyl (e.g. 1,5-naphthylidin-2- or 3-yl), thieno[2,3-d]pyridyl (e.g. thieno[2,3-d]pyridin- 3-yl), pyrazinoquinolyl (e.g. pyrazino[2,3-d]-quinolin- 2-yl) and chromenyl (e.g. 2H-chromen-2 or 3yl). The aforesaid acyl group is an acyl group derived from an organic carboxylic group, such as an alkanoyl group, preferably containing 1 to 7 carbon atoms (e.g. formyl, acetyl, propionyl, butyryl, isobutyryl, pentanoyl, hexanoyl or heptanoyl), an arylcarbonyl group, preferably containing 6 to 14 carbon atoms (e.g. benzoyl or naphthalenecarbonyl), an alkoxycarbonyl group, preferably containing 1 to 6 carbon atoms (e.g. methoxycarbonyl, ethoxycarbonyl, propoxycarbonyl, isopropoxycarbonyl, butoxycarbonyl, isobutoxycarbonyl, sec-butoxycarbonyl or tert- butoxycarbonyl), an aryloxycarbonyl group, preferably containing 7 to 14 carbon atoms (e.g. phenoxycarbonyl), an aralkylcarbonyl group, preferably containing 7 to 19 carbon atoms (e.g. benzylcarbonyl, phenethylcarbonyl, phenylpropylcarbonyl, benzhydrylcarbonyl or naphthylethyl carbonyl), a 5- or 6-membered heterocyclic-carbonyl group containing 1 to 4 hetero atoms, such as nitrogen (which may be oxidized), oxygen and sulfur which may be mono or dioxidized (e.g. 2-, 3- or 4-pyrrolylcarbonyl, 3-, 4- or 5-pyrazolylcarbonyl, 2-, 4- or 5-imidazolylcarbonyl, 1,2,3-triazol-4-ylcarbonyl, 1,2,4-triazol-3-ylcarbonyl, 1H- or 2H-tetrazol- 5-ylcarbonyl, 2- or 3-furylcarbonyl, 2- or 3-thienylcarbonyl, 2-, 4- or 5-oxazolylcarbonyl, 3-, 4- or 5-isoxadiazol-4- or 5-ylcarbonyl, 1,2,4-oxadiazol-3- or 5-ylcarbonyl, 1,2,5-oxadiazol-3 or 4-ylcarbonyl, 1,3,4-oxadiazol-2 or 5-ylcarbonyl, 2-, 4- or 5-thiazolylcarbonyl, 3-, 4- or 5-isothiazolylcarbonyl, 1,2,3-thiadiazol-4 or 5-ylcarbonyl, 1,2,4-thiadiazol-3 or 5-ylcarbonyl, 1,2,5-thiadiazol-3 or 4-ylcarbonyl, 1,3,4-thiadiazol-2 or 5-ylcarbonyl, 2- or 3-pyrolidinylcarbonyl, 2-, 3- or 4-pyridylcarbonyl, 2-, 3- or 4-pyridyl-N-oxido-carbonyl, 3- or 4-pyridazinylcarbonyl, 3- or 4-pyridazinyl-N-oxido-carbonyl, 2-, 4- or 5-pyrimidinylcarbonyl, 2-, 4- or 5-pyrimidinyl-N-oxido-carbonyl, pyrazinylcarbonyl, 2-, 3- or 4-piperidinylcarbonyl, piperazinylcarbonyl, 3H-indol-2 or 3-ylcarbonyl, 2-, 3- or 4-pyranylcarbonyl, 2-, 3- or 4-thiopyranylcarbonyl, 3-, 4-, 5-, 6-, 7- or 8-quinolylcarbonyl, pyrido[2,3-d]pyrimidinylcarbonyl (e.g. pyrido[2,3-d]pyrimidin-2-ylcarbonyl), 1,5-, 1,6-, 1,7-, 1,8-, 2,6- or 2,7-naphthylidinylcarbonyl (e.g. 1,5-naphthylidin-2- or 3-ylcarbonyl), thieno[2,3-d]pyridylcarbonyl (e.g. thieno[2,3-d]pyridin-3-ylcarbonyl), pyrazinoquinolylcarbonyl (e.g. pyrazino[2,3-b]quinolin-2-ylcarbonyl), chromenylcarbonyl (e.g. 2H-chromen-2- or 3-ylcarbonyl), a 5- or 6-membered heterocyclic-acetyl group containing 1 to 4 hetero atoms such as nitrogen which may be oxidized), oxygen or sulfur which may be mono- or dioxidized) (e.g. 2-pyrrolylacetyl or 3-imidazolylacetyl, 5-isoxazolylacetyl).

Examples of the group of the formula —T—Q₀ include an alkoxy, alkenyloxy, aryloxy, aralkyloxy, heterocyclic-oxy, acyloxy, alkylthio, alkenylthio, arylthio, aralkylthio, heterocyclethio, acylthio, alkyldithio, aryldithio, aralkyldithio, alkylsulfinyl, alkenylsulfinyl, arylsulfinyl, aralkylsulfinyl, heterocyclesulfinyl, alkylsulfonyl, alkenylsulfonyl, arylsulfonyl, aralkylsulfonyl and heterocyclic-sulfonyl.

The alkoxy group mentioned above is a straight-chain, branched or cyclic alkoxy group preferably containing 1 to 6 carbon atoms, such as methoxy, ethoxy, n-propoxy, isopropoxy, n-butoxy, isobutoxy, sec-butoxy, tert-butoxy, n-pentyloxy, sec-pentyloxy, isopentyloxy, neopentyloxy, cyclopentyloxy, n-hexyloxy, isohexyloxy or cyclohexyloxy. The alkenyloxy group is a straight-chain, branched or cyclic alkenyloxy group preferably containing 3 to 6 carbon atoms, such as allyloxy, isopropenyloxy, 1-butenyloxy, 2-pentenyloxy or 2-hexenyloxy. The aryloxy group is preferably an aryloxy group containing 6 to 14 carbon atoms, such as phenoxy, naphthyloxy or biphenylyloxy. The aralkyloxy group is preferably an aralkyloxy group containing 7 to 19 carbon atoms, such as benzyloxy, phenethyloxy or phenylpropyloxy. The heterocyclic-oxy group is a group of the formula T'—O— (T' is a heterocyclic group as mentioned above), such as 2- or 3-pyrrolyloxy, 3-, 4- or 5-pyrazolyloxy, 2-, 4- or 5-imidazolyloxy, 1,2,3-triazol-4-yloxy, 1,2,4-triazol-3-yloxy, 1H- or 2H-tetrazol-5-yloxy, 2- or 3-furyloxy, 2 or 3-thienyloxy, 2- or 3-thienyloxy-1,1-dioxido or 2-, 4- or 5-oxazolyloxy. The acyloxy group is a group of the formula T"—O— (T" is an acyl group as mentioned hereinbefore), such as acetoxy, propionyloxy, butyryloxy, pentanoyloxy, hexanoyloxy, benzylcarbonyloxy, phenethylcarbonyloxy, benzoyloxy, naphthoyloxy, thienylcarbonyloxy or benzothienylcarbonyloxy. The alkylthio group is a straight-chain, branched or cyclic alkylthio group preferably containing 1 to 6 carbon atoms, such as methylthio, ethylthio, n-propylthio, isopropylthio, n-butylthio, isobutylthio, sec-butylthio, tert-butylthio, n-pentylthio, sec-pentylthio, isopentylthio, neopentylthio, cyclopentylthio, n-hexylthio or isohexylthio, cyclohexylthio. The alkenylthio group is a straight-chain, branched or cyclic alkenylthio group preferably containing 3 to 6 carbon atoms, such as allylthio, isopropenylthio, 1-butenylthio, 2-pentenylthio or 2-hexenylthio. The arylthio group is preferably an arylthio group containing 6 to 14 carbon atoms, such as phenylthio, naphthylthio or biphenylthio. The aralkylthio group is preferably an aralkylthio group of 7 to 19 carbon atoms, such as benzylthio, phenethylthio or phenylpropylthio. The heterocyclic-thio group is a group of the formula T'—S— (T' is a heterocyclic group as mentioned hereinbefore), such as 2- or 3-pyrrolylthio, 3-, 4- or 5-pyrazolylthio, 2-, 4- or 5-imidazolylthio, 1,2,3-triazol-4-ylthio, 1,2,4-triazol-5-ylthio, 1H- or 2H-tetrazol-5-ylthio, 2- or 3-furylthio, 2- or 3-thienylthio, 2- or 3-thienylthio-1,1-dioxido or 2-, 4- or 5-oxazolylthio. The acylthio group is a group of the formula T"—S— (T" is an acyl group as mentioned hereinbefore), such as acethylthio, propionylthio, butyrylthio, pentanoylthio, hexanoylthio, benzylcarbonylthio, phenethylcarbonylthio, benzoylthio, nephthoylthio, thienylcarbonylthio or benzothienylcarbonylthio. The alkyldithio group is a straight-chain, branched or cyclic alkyldithio group preferably containing 1 to 6 carbon atoms, such as methyldithio, ethyldithio, n-propyldithio or cyclopentyldithio. The aryldithio group is preferably an aryldithio group containing 6 to 14 carbon atoms, such as phenyldithio, naphthyldithio or biphenylyldithio. The aralkyldithio group is preferably an aralkyldithio group containing 7 to 19 carbon atoms, such as benzyldithio or phenethyldithio. The alkylsulfinyl group is a straight-chain, branched or cyclic alkylsulfinyl group preferably containing 1 to 6 carbon atoms, such as methylsulfinyl, ethylsulfinyl, n-propylsulfinyl, n-hexylsulfinyl or cyclohexylsulfinyl. The alkenylsulfinyl group is a straight-chain, branched or cyclic alkenylsulfinyl group preferably containing 3 to 6 carbon atoms, such as allylsulfinyl. The arylsulfinyl group is preferably an arylsulfinyl group containing 6 to 14 carbon atoms, such as phenylsulfinyl. The aralkylsulfinyl group is preferably a aralkylsulfinyl group containing 7 to 19 carbon atoms, such as benzylsulfinyl. The heterocyclic-sulfinyl group is a group of the formula T'—SO— (T' is a heterocyclic group as mentioned hereinbefore), such as 2- or 3-pyrrolylsulfinyl or 3-, 4- or 5-pyrazolylsulfinyl. The alkylsulfonyl group is a straight-chain, branched or cyclic alkylsulfonyl group preferably containing 1 to 6 carbon atoms, such as methylsulfonyl, ethylsulfonyl or cyclohexylsulfonyl. The alkenylsulfonyl group is a straight-chain, branched or cyclic alkenylsulfonyl group preferably containing 3 to 6 carbon atoms, such as allylsulfonyl. The arylsulfonyl group is preferably an arylsulfonyl group containing 6 to 14 carbon atoms, such as phenylsulfonyl, naphthylsulfonyl or biphenylylsulfonyl. The aralkylsulfonyl group is preferably an aralkylsulfonyl group containing 7 to 19 carbon atoms, such as benzylsulfonyl, phenethylsulfonyl or phenylpropylsulfonyl. The heterocyclic-sulfonyl group is a group of the formula T'—SO₂— (T' is a heterocyclic group as mentioned hereinbefore), such as 2- or 3-pyrrolylsulfonyl or 3-, 4- or 5-pyrazolylsulfonyl.

The group of the formula

may be an alkylamino group, preferably a mono- or di-($C_{1-6}$ alkyl)amino group, such as methylamino, ethylamino, n-propylamino, n-butylamino, tert-butylamino, n-pentylamino, n-hexylamino, dimethylamino, diethylamino, methylethylamino, di-(n-propyl)amino or di-(n-butyl)amino, a cycloalkylamino group, preferably a mono- or di-(a cycloalkyl group containing 3 to 6 carbon atoms)amino group, such as cyclopropylamino, cyclopentylamino, cyclohexylamino or dicyclohexylamino; an arylamino group, preferably an arylamino group containing 6 to 14 carbon atoms, such as anilino or N-methylanilino; an aralkylamino group, preferably an aralkylamino group containing 7 to 19 carbon atoms, such as benzylamino, 1-phenylethylamino, 2-phenylethylamino, benzhydrylamino or tritylamino; an acylamino group which is a group of the formula T"—NH— or (T")$_2$N— (T" is an acyl group as mentioned hereinbefore; the two T" groups taken together with the nitrogen atom may form a ring), such as alkylcarbonylamino, arylcarbonylamino, heterocycliccarbonylamino (the alkyl, aryl and heterocyclic groups are preferably those mentioned hereinbefore) or cyclic imido, for example acetamido, propionamido, butyrylamino, pentanoylamino, hexanoylamino, succinimido, benzylcarbonylamino (benzylcarboxamido), phenethylcarbonylamino (phenethylcarboxamido), benzoylamino (benzamido), naphthoylamino, phthalimido, thienylcarbonyl,amino (thienylcarboxamido) or benzothienylcarbonylamino (benzothienylcarboxamido).

Concrete example of the group of the formula

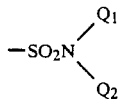

include a mono- or dialkylsulfamoyl group, preferably a mono- or di-alkylsulfamoyl group containing 1 to 6 carbon atoms, such as methylsulfamoyl, ethylsulfamoyl, n- propylsulfamoyl, n-hexylsulfamoyl, dimethylsulfamoyl, diethylsulfamoyl, methylethylsulfamoyl, di-(n-butyl)sulfamoyl; a cycloalkylsulfamoyl group, preferably a cycloalkylsulfamoyl group containing 3 to 6 carbon atoms, such as cyclopropylsulfamoyl, cyclohexylsulfamoyl; an arylsulfamoyl group, preferably an arylsulfamoyl group containing 6 to 14 carbon atoms, such as phenylsulfamoyl; an aralkylsulfamoyl group, preferably an aralkylsulfamoyl group containing 7 to 19 carbon atoms, such as benzylsulfamoyl, 1-phenylethylsulfamoyl, 2-phenylethylsulfamoyl, benzhydrylsulfamoyl or tritylsulfamoyl; and an acylsulfamoyl group of a group of the formula T"—NHSO$_2$— or (T")$_2$N—SO$_2$— (T" is an acyl group as mentioned hereinbefore), such as acetylsulfamoyl, benzylcarbonylsulfamoyl or thienylcarbonylsulfamoyl. Examples of the group of the formula Q$_2$—SO$_2$—O include an alkylsulfonyloxy group, preferably an alkylsulfonyloxy group containing 1 to 6 carbon atoms, such as methanesulfonyloxy or ethanesulfonyloxy; an arylsulfonyloxy group, preferably an arylsulfonyloxy group containing 6 to 14 carbon atoms, such as benzenesulfonyloxy or p-toluenesulfonyloxy; an aralkylsulfonyloxy group, preferably an aralkylsulfonyloxy group containing 7 to 19 carbon atoms, such as benzylsulfonyloxy or phenethylsulfonyloxy; and an acylsulfonyloxy group, such as acetylsulfonyloxy or butyrylsulfonyloxy.

The aforementioned alkyl, alkoxy, alkylthio, alkyldithio, alkylsulfinyl, alkylsulfonyl, alkylamino, cycloalkylamino, alkenyl, alkenyloxy, alkenylthio, alkenyldithio, alkenylsulfinyl, alkenylsulfonyl, alkynyl, alkoxycarbonyl, alkanoyl, and alkylsulfonyloxy groups may further be substituted by 1 to 3 substituents, such as alkylthio (e.g. a straight-chain or branched alkylthio group containing 1 to 4 carbon atoms, such as methylthio, ethylthio, n-propylthio or isobutylthio), halogen (e.g. fluorine, chlorine, bromine or iodine), alkoxy (e.g. a straight-chain or branched alkoxy group containing 1 to 6 carbon atoms, such as methoxy, ethoxy, n-propoxy, tert-butoxy or n-hexyloxy), nitro, an alkoxycarbonyl group (e.g. alkoxycarbonyl groups containing 1 to 6 carbon atoms, such as methoxycarbonyl, ethoxycarbonyl, n-propoxycarbonyl, isopropoxycarbonyl, n-butoxycarbonyl, isobutoxycarbonyl, sec-butoxycarbonyl or tert-butoxycarbonyl), an alkylamino group (e.g. mono- or di-(alkyl of 1 to 6 carbon atoms)amino groups, such as methylamino, ethylamino, n-propylamino, n-butylamino, tert-butylamino, n-pentylamino, n-hexylamino, dimethylamino, diethylamino) methylethylamino, di-(n-propyl)amino or di-(n-butyl)amino).

Where two alkoxy groups are present as substituents, they may combined to form an alkylenedioxy group containing 1 to 3 carbon atoms, such as methylenedioxy, ethylenedioxy or propylenedioxy, or an alkylidenedioxy group containing 2 to 6 carbon atoms, such as ethylidenedioxy, propylidenedioxy or isopropylidenedioxy.

The aforementioned aryl, aryloxy, aryloxycarbonyl, arylcarbonyl, arylthio, aryldithio, arylsulfinyl, arylsulfonyl, arylamino, aralkyloxy, aralkyloxycarbonyl, aralkylthio, aralkyldithio, aralkylsulfinyl, aralkylsulfonyl, aralkylamino, aralkylcarbonyl, arylsulfonyloxy and aralkylsulfonyloxy groups may be further substituted on their aromatic ring by 1 to 3 substituents, such as alkyl, alkenyl, alkynyl, alkoxy, acyl, acyloxy, nitro, cyano, halogen, acylamino or alkylthio. Here the same alkyl, alkenyl, alkynyl, alkoxy, acyl, acyloxy, acylamino, halogen and alkylthio as mentioned above are used.

Where two alkyl groups are present in adjacent positions, they may be combined to form a bivalent group, such as trimethylene, tetramethylene, and where two alkenyl groups are present in adjacent positions, they may be combined to form a bivalent group, such as propenylene, 1-butenylene, 2-butenylene or butadienylene.

In such cases, the bivalent group may form a 5- or 6-membered alicyclic ring (e.g. cyclopentane, cyclohexane or cyclohexadiene), an aromatic ring (e.g. benzene) or a 5- or 6-membered heterocyclic ring containing 1 to 4 hetero atoms, such as nitrogen, oxygen or sulfur.

Of the aforementioned organic residues, preferred are (1) an alkyl group which may be substituted by the same or different 1 to 3 substituents of halogen, alkylthio or alkoxy, (2) an aryl group, (3) an alkylthio group, (4) an alkenylthio group, (5) an alkylsulfinyl group, (6) an alkylsulfonyl group, (7) an alkenylsulfonyl group, (8) an alkoxycarbonyl groups, (9) carbamoyl, (10) butadienylene, (11) an alkylamino group and (12) an alkoxy group.

The heterocyclic-oxy, heterocyclic-thio, heterocyclic-sulfinyl, heterocyclic-carbonyl, and heterocyclic-sulfonyl groups mentioned above may be substituted by 1 to 3 of the aforementioned alkyl, alkenyl, alkynyl, aryl, aralkyl, alkanoyl, arylcarbonyl, alkoxycarbonyl, aryloxycarbonyl, aralkylcarbonyl, nitro, amino, hydroxy, cyano, sulfamoyl, mercapto and/or halogen (e.g. fluorine, chlorine, bromine or iodine).

The substituent on the condensed heterocyclic group having a nitrogen atom in the bridgehead position is preferably halogen, a straight or branched-chain alkyl group of 1 to 6 carbon atoms or a straight or branched-chain alkoxy group of 1 to 6 carbon atoms. Among these, chlorine, methyl, methoxy, ethoxy and isopropoxy are preferable. Chlorine is more preferable.

Q is preferably a group of the general formula

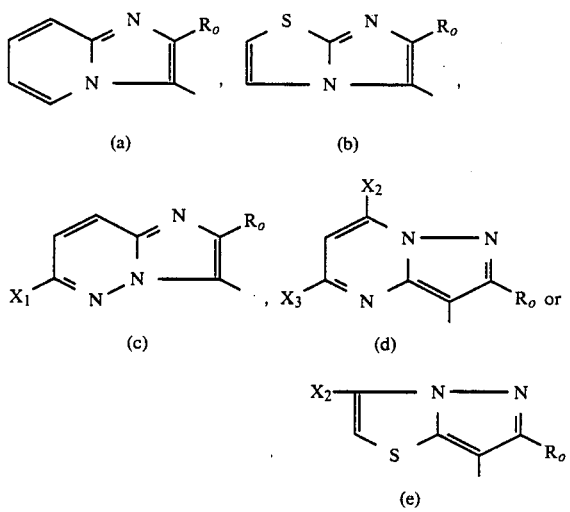

wherein $R_0$ is hydrogen, a lower alkyl group which may optionally be substituted by halogen, a lower alkylthio group, a lower alkylsulfonyl group, a lower alkoxycarbonyl group or halogen; $X_1$ is hydrogen, halogen or a lower alkoxy, lower alkylthio, lower alkylamino or di-(lower alkyl)amino group; $X_2$ and $X_3$ each is hydrogen or a lower alkyl group. Preferred are groups of formulas (a), (b) and (c).

$R_0$ is preferably halogen or a lower alkyl group which may be substituted by halogens. $X_1$ is preferably a lower alkoxy group.

Here, the lower alkyl group and the lower alkyl moiety of lower alkyl group which may optionally substituted by halogen, lower alkylthio group, lower alkylsulfonyl group, lower alkylamino group or di-lower alkylamino group include an alkyl group containing 1 to 4 carbon atoms (e.g. methyl, ethyl, n-propyl, isopropyl, n-butyl or t-butyl). The lower alkoxy group is an alkoxy group containing 1 to 4 carbon atoms (e.g. methoxy, ethoxy, propoxy, isopropoxy or t-butoxy). The halogen and the halogen of the optionally halogen-substituted lower alkyl group include fluorine, chlorine and bromine, preferably chlorine.

The alkyl group represented by $Y_2$ is preferably a straight-chain or branched alkyl group containing 1 to 6 carbon atoms, such as methyl, ethyl, n-propyl, isopropyl, n-butyl, isobutyl, sec-butyl, tert-butyl, n-pentyl, sec-pentyl, isopentyl, neopentyl, n-hexyl or isohexyl.

The halogen represented by $Y_1$ includes fluorine, chlorine, bromine and iodine, preferably chlorine.

The alkyl group represented by $R_1$ or $R_2$, is preferably a straight-chain, branched or cyclic alkyl group preferably containing 1 to 6 carbon atoms, such as methyl, ethyl, n-propyl, isopropyl, n-butyl, isobutyl, sec-butyl, tert-butyl, n-pentyl, sec-pentyl, isopentyl, neopentyl, cyclopentyl, n-hexyl, isohexyl or cyclohexyl. The alkoxy group represented by $R_1$ or $R_2$ is preferably a straight-chain or branched alkoxy group containing 1 to 6 carbon atoms, such as methoxy, ethoxy, n-propoxy, isopropoxy, n-butoxy, isobutoxy, sec-butoxy, tert-butoxy, n-pentyloxy or n-hexyloxy. The halogen represented by $R_1$ or $R_2$ is, for example, fluorine, chlorine, bromine or iodine.

$R_1$ and $R_2$ each are preferably a lower alkyl group (e.g. an alkyl group of 1 to 4 carbon atoms, such as methyl, ethyl, n-propyl, isopropyl, n-butyl, tertbutyl, etc.), a lower alkoxy group (e.g. an alkoxy group of 1 to 4 carbon atoms, such as methoxy, ethoxy, n-propoxy, isopropoxy, n-butoxy, tert-butoxy) or halogen (e.g. fluorine, chlorine or bromine). More preferably, $R_1$ and $R_2$ each are methyl, methoxy or chlorine. Most preferably $R_1$ and $R_2$ each are methyl or methoxy, especially methoxy. Z is preferably CH.

The compounds (I), (IV) and (V) may each form a salt with an organic or inorganic base through an acid group, such as sulfo or carboxyl, in the substituent. The compounds (I), (II), (IV) and (V) may each form an organic or inorganic acid addition salt through a basic nitrogen atom within its molecule and a basic group, such as amino in its substituent. The compounds (I) and (V) contain an acid group

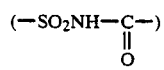

and may, therefore, form a salt with an organic or inorganic or base.

Examples of the inorganic base salts of compound (I), (IV) and (V) include salts with an alkali metal (e.g. sodium or potassium), an alkaline earth metal (e.g. calcium) and ammonia. Examples of the organic base salts of compound (I), (IV) and (V) include salts with dimethylamine, triethylamine, piperazine, pyrrolidine, piperidine, 2-phenylethylbenzylamine, benzylamine, ethanolamine and diethanolamine.

Examples of the inorganic acid addition salt of compounds (I), (II), (IV) and (V) include salts with hydrochloric acid, hydrobromic acid, sulfuric acid, nitric acid and phosphoric acid. Examples of the organic acid addition salts of compounds (I), (II), (IV) and (V) include salts with p-toluenesulfonic acid, methanesulfonic acid, formic acid and trifluoroacetic acid.

In this specification, compounds (I), (II), (IV) and (V) are mentioned as meaning the salts as well.

The compound (I) is prepared by reacting a compound (IV) with the compound (III) in the presence of a base (the first step) and, then, allowing the compound (II) and an acid to act on the reaction product in the reaction mixture of the first step under anhydrous conditions (the second step).

In the first step the reaction, the starting compound (III) is used in a proportion of about 0.5 to 2 molar equivalents, preferably about 0.8 to 1.2 molar quivalents, relative to 1 mole of compound (IV).

The compound (III) wherein $Y_1$ is halogen; and $Y_2$ is phenyl is preferable.

Concrete examples of the starting compound (III) include phenyl chloroformate, methyl chloroformate, ethyl chloroformate, isopropyl chloroformate, diphenyl carbonate, dimethyl carbonate, diethyl carbonate, di-2-tolyl carbonate, di-4-tolyl carbonate, di-(α-naphthyl)-carbonate and bis(4-chlorophenyl)carbonate, preferably phenyl chloroformate.

The base includes alkali metal hydroxides, such as sodium hydroxide or potassium hydroxide, alkali metal carbonates, such as sodium carbonate or potassium carbonate, alkali metal hydrogen carbonates, such as sodium hydrogen carbonate, alkoxides, such as sodium methoxide, sodium ethoxide or potassium t-butoxide, and organic tertiary amines, such as pyridine, lutidine, triethylamine, diisopropylethylamine, tripropylamine, tributylamine, N,N-dimethylaniline, N,N-diethylaniline, 1,8-diazabicyclo[5,4,0]-7-undecene or 1,4-diazabicyclo[2,2,2]octane. Preferred bases are organic tertiary amines. More preferred is triethylamine. The base is used in a proportion of about 1 to 2.1 molar equivalents relative to the compound (III).

More concretely, the base is preferably used in an amount of about 1.8 to 2.1 moles per 1 mole of the compound (III) wherein $Y_1$ is halogen, and about 1 to 2.0 moles per the compound (III) wherein $Y_1$ is $OY_2$.

This reaction is conducted in a solvent which does not interfere with the reaction. Examples of the solvent include organic solvents exemplified by aliphatic hydrocarbons such as petroleum ether, ligroin or petroleum benzine, aromatic hydrocarbons such as benzene, toluene or xylene, halogenated hydrocarbons such as dichloromethane, chloroform, carbon tetrachloride, trichloroethylene or chlorobenzene, ethers such as diethyl ether, methyl ethyl ether, diisopropyl ether, dibutyl ether, propylene oxide, dioxane, tetrahydrofuran or ethylene glycol monomethyl ether, nitriles such as acetonitrile or propionitrile, ketones such as acetone, methyl isobutyl ketone or methyl ethyl ketone, esters such as ethyl acetate or butyl acetate, acid amides such as dimethylformamide or dimethylacetamide, dimethyl sulfoxide and sulfolane.

Preferred solvents are halogenated hydrocarbon and nitriles. More preferred solvents are acetonitrile and dichloromethane.

The reaction temperature is about −20° C. to 150° C., preferably about 5° to 100° C.

The reaction time is comparatively short and generally within the range of about 5 minutes to about one hour. In conducting the reaction of 1st step, the compound (III) may be added to the solution of base and compound (IV) in the solvent, or the base may be added to the solution of compounds (III) and (IV) in the solvent.

The reaction of this first step gives the compound (V) in the reaction mixture. The resultant compound (V) is directly subjected to the second step of reaction without isolation from the reaction mixture.

In the second step of reaction, the compound (II) is used in about equimolar amount per the compound (III). As the acid in this reaction use may be made of an inorganic acid, e.g. hydrogen chloride, hydrogen bromide, sulfuric acid, etc., methanesulfonic acid, ethanesulfonic acid, benzenesulfonic acid, an acid ion exchange resin or the like. Preferably hydrogen chloride, hydrogen bromide, sulfuric acid, methanesulfonic acid and ethanesulfonic acid are employed. In case of hydrogen chloride or hydrogen bromide, it may be used as previously dissolved in the above-mentioned organic solvent.

The amount of acid depends on the amount of base used in the 1st step and the species of compound (III). For example, in the case that the compound (III) wherein $Y_1$ is halogen, the acid is used in an amount of about 0.4 to 0.6 moles per the base. When the compound (III) wherein $Y_1$ is $OY_2$ is empolyed, the acid is used in an amount of about 0.9 to 1.1 moles per the base.

This reaction is conducted under anhydrous condition. Since contamination of the reaction mixture with water interferes with the reaction, any water is preferably eliminated from the reaction system. The solvent may be the same solvent as used in the first step of reaction. The order of adding the acid and the compound (II) is arbitrary.

The reaction proceeds at a temperature of about 10° C. to about 100° C. The reaction time depends on the reaction temperature, but is generally within the range of about 10 minutes to 6 hours. Concretely, the reaction time is about 10 minutes to 2 hours in the case that the reaction temperature is about 50 to 100° C., and about 2 to 6 hours in the case that the reaction temperature is about 10° C. to lower than 50° C.

The reaction product can be isolated and purified by the per se known procedures such as solvent extraction, pH adjustment, distillation, distillation under reduced pressure, concentration under reduced pressure, phase transfer crystallization, recrystallization or chromatography.

For example, the resulting reaction mixture is cooled, and thereby crystals which separate out are collected by filtration, or after subjecting the resulting reaction mixture to concentration under reduced pressure, the solvent is added to the residue, and crystals which separate are collected by filtration.

The compound (I) exerts in extremely low application amount, potent herbicidal activity against a broad range of weeds, for example, paddy weeds such as *Echinochloa oryzicola, Cyperus difformis, Scirpus juncoides, Monochoria vaginalis, Sagittaria pygmaea, Eleocharis acicularis, Cyperus serotinus, Eleocharis kuroguwai, Alisma canaliculatum, Sagittaria trifolia, Scirpus wallichii, Lindernia procumbens, Rotala indica, Potamogeton distinctus, Ludwiga prostrata* or *Flatine triandra*, and field weeds, such as *Digitaria adscendens, Setaria viridis, Amaranthus viridis, Abutilon theophrasti, Chenopodium album, Polygonum longisetum, Portulaca oleracea, Sida spinosa, Datura stramonium, Ipomoea purpurea, Xanthium strumarium, Echinochloa crus-galli, Panicum dichotaomiflorum, Sorghum halepense, Cyperus rotundus, Avena fatua, Alopecurus mvosuroides, Bromus tectorum, Stellaria media, Brassica Sp., Cassia obtusifolia, Matricaria chamomilla* or *Commelina communis*. Moreover, they exhibit substantially no damage on crops such as rice, wheat, barley, corn, soybean, etc. and show a high grade of safety.

The compounds (I) exhibit an excellent herbicidal effect selectively on various weeds only, and not on crops, and are only slightly toxic to mammals, fish and shellfish. Therefore, they can be used as herbicides for paddy field, field (farm field), orchard or non-farming land, in extremely high safety, without polluting the environment.

The compounds (I) can be used as herbicides in any application form suited for general agricultural chemicals. That is, one, two, or more than two kinds of the compound (I) is used in the form of preparation such as emulsifiable concentrates, oil solution, sprays, wettable powders, dusts, DL(Driftless)-type dusts [c.f. Journal of Pesticide Science, 7, 403 to 408 (1982)], granules, fine granules, micro-granules fine [c.f. Journal of Pesticide Science 7, 403 to 408 (1982)], or tablets, according to the purpose of use, by dissolving or dispersing them in suitable liquid carriers or mixing them with or adsorbing them on suitable solid carriers. These preparations may contain, in necessary, emulsifying agent, suspending agent, spreading agent, penetrating agent, wetting agent, thickening agent, stabilizer, etc., and can be prepared by any conventional method known per se., e.g. mixing each ingredients.

Suitable examples of the liquid carriers (solvents), include solvents such as water, alcohols (for example, methanol, ethanol, n-propanol, isopropanol or ethylene glycol), ketones (for example, acetone or methyl ethyl ketone), ethers (for example, dioxane, tetrahydrofuran, ethylene glycol monomethyl ether, diethylene glycol monomethyl ether or propylene glycol monomethyl ether), aliphatic hydrocarbons (for example, kerosine, kerosene oil, fuel oil or machine oil), aromatic hydrocarbons (for example, benzene, toluene, xylene, solvent naphtha or methylnaphthalene), halogenated hydrocarbons (for example, dichloromethane, chloroform or carbon tetrachloride), acid amides (for example, dimethylformamide or dimethylacetamide), esters (for example, ethyl acetate, butyl acetate or fatty acid glycerol ester) or nitriles (for example, acetonitrile or propionitrile). These solvents are used individually or as a suitable mixture of two, or more, of them.

Suitable examples of the solid carriers (diluents or dust carrier) include vegetable powder (for example, soybean meal, tobacco meal, wheat flour or wood flour, mineral powders (for example, clays such as kaolin, bentonite, or acid clay, talcs such as talc powder or pyrophyllite powder), silicas (for example, diatomaceous earth or mica powder), aluminas, sulfur powder or active carbon are suitably used. They are used individually or as a suitable mixture of two, more, of them.

As surface active agents used as the emulsifying agent, spreading agent, penetrating agent or dispersing agent, if necessary, use can be made of nonionic or anionic surface active agents, such as soaps; polyoxyethylene alkylaryl ethers (e.g. Noigen EA 142 ® from Dai-ichi Kogyo Seiyaku K. K., Japan); polyoxyethylene aryl esters (e.g. Nornal ® from Toho Chemical K. K., Japan); alkylsulfates (e.g. Emal 10 ® and Emal 40 ® from Kao Soap K. K., Japan); alkyl sulfonates (e.g. Neogen ® and Neogen T ® from Dai-ichi Kogyo Seiyaku Co. and Neopelex ® from Kao Soap K. K.); polyethylene glycol ethers (e.g. Nonipol 85 ®, Nonipol 100 ®, Nonipol 160 ® from Sanyo Kasei K. K., Japan); or polyhydric alcohol esters (e.g. Tween 20 ® and Tween 80 ® from Kao Soap K. K.).

The amount of the compound (I) contained in the herbicidal preparation is suitably about 1 to 90% by weight in the case of emulsifiable concentrates or wettable powders, about 0.01 to 10% by weight in the case of oil solution, dusts or DL-type dusts and about 0.05 to 10% by weight in the case of fine granules F or granules. However, such concentration may be changed properly, depending on the purpose of use. Emulsifiable concentrates, wettable powders or the like are suitably diluted or extended (for example, to 100 to 100000 times) with water or the like, on the occasion of use, and then scattered.

When the compound (I) is used as herbicide, its amount may vary depending on the place, the season and the method of application, the kinds of target weeds, the kinds of culture crops, and so on. However, an active ingredient (the compound (I)) is used in general, in an amount of about 0.05 to 50 g, preferably about 0.1 to 5 g, per are of paddy field and in an amount of about 0.05 to 20 g, preferably about 0.1 to 5 g, per are of field.

For paddy field weeds, it is suitable to use the compound (I) in the soil treatment before germination or in the cormophyte and soil treatment.

For example, the herbicidal preparation can be used in safety just after the rice-planting or even 2 to 3 weeks after the planting without revealing any harmful effect, and its effect on the rice continues for a long period of time.

The herbicidal preparation can be used, as occasion demands, in combination with or as an admixture with other herbicidal agent, plant-growth regulating agent, fungicidal agent (for example, organochlorine series fungicide, organosulfur series fungicide or azole series fungicide, antibiotics), insecticidal agent (for example, pyrethroid series insecticide, organophosphorus series insecticide or carbamate series insecticide), and also with miticide, nematocide, synergist, attractant, repellent, dyestuff, fertilizer and the like.

The starting compounds (II), (III) and (IV) of the invention are known or can be easily prepared from known compounds.

For example, compound (II) can be prepared by the method described, for example, in The Chemistry of Heterocyclic Compounds (Interscience Publishers, New York & London) 16, (1962), and Journal of Organic Chemistry 28, 1812–1821, (1963) or by processes analogous thereto.

The compound (IV) can be easily prepared by producing a compound (VI) or a salt thereof in accordance with the following reaction schemas (1)–(4) and, then, reacting the compound (VI) or salt with ammonia.

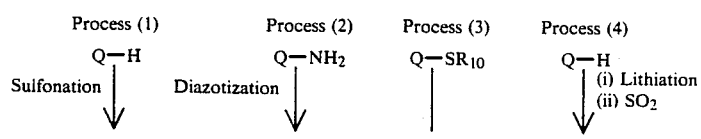

-continued

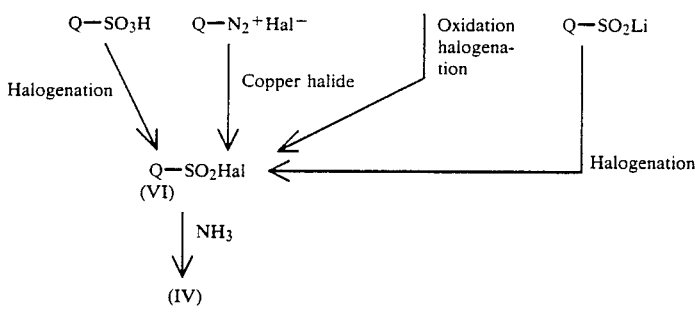

[wherein Hal is halogen; $R_{10}$ is hydrogen, benzyl or S—Q; the other symbols are as defined hereinbefore]

The halogen represented by Hal is for example be fluorine, chlorine or bromine.

The compound represented by the above formula can be used in the form of salt with a base or as an acid addition salt as mentioned above.

Concrete examples of the above process (1) are:

(a)
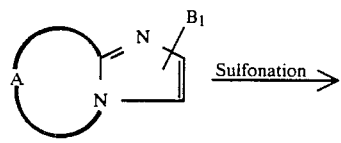
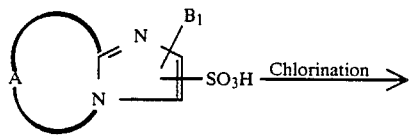
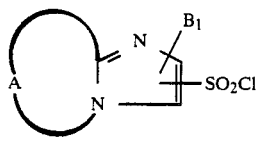

(b)
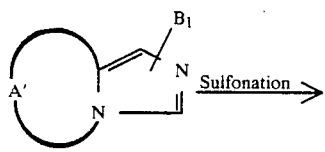
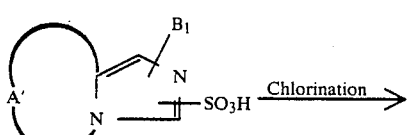
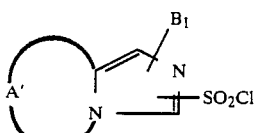

(c)
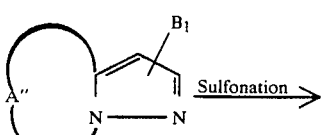
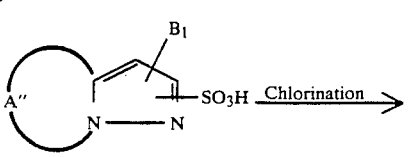

-continued (d)
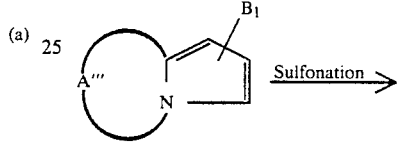
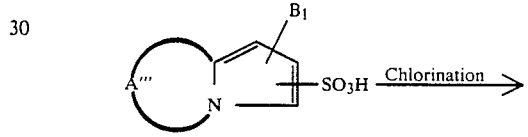

(e)

[wherein the symbols are as defined hereinbefore]
Concrete examples of process (2) are:

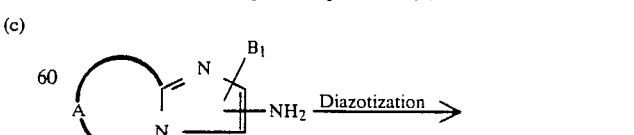
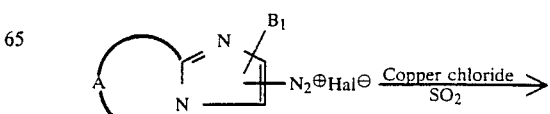

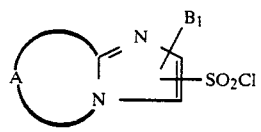

[wherein the symbols are as defined hereinbefore]
Concrete examples of process (3) are:

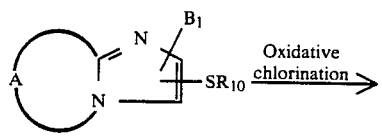 (a)

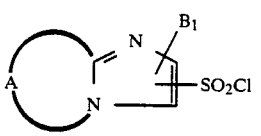

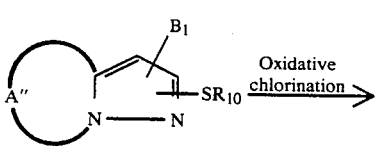 (b)

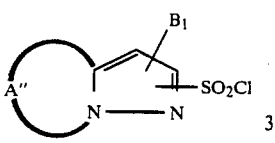

[wherein the symbols are as defined hereinbefore]
Specific examples of process (4) are:

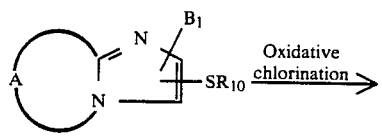 (a)

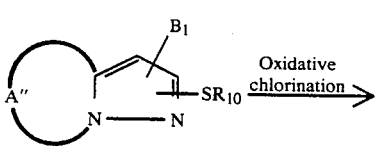

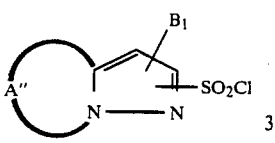

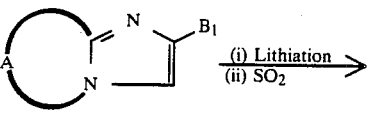 (b)

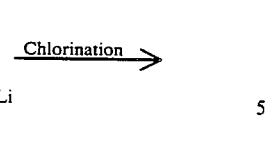

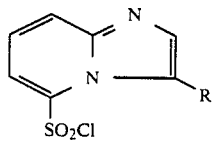

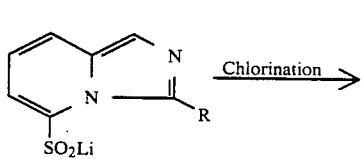 (c)

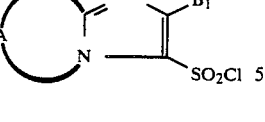

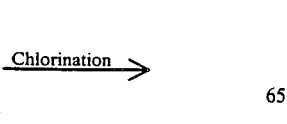

[wherein the symbols are as defined hereinbefore].

The reactions involved in the processes (1) through (4) producing for compound (VI) or a salt thereof are per se known and can be carried out in accordance with the procedures described in Methoden der Organischen Chemie Vol. 9, (1955), Sulfonation and Related Reactions, Interscience Publishers, New York, 1965, Synthesis, 1969, p.3–10, Japanese Published Unexamined Patent Application No. 208977 (1985), etc. or by procedures analogous thereto. The compound (VI) or a salt thereof is produced by the following processes.

Process (1)

In the sulfonation reaction a sulfonating agent, such as sulfuric acid, fuming sulfuric acid or chlorosulfonic acid is employed. The sulfonating agent is used in a proportion of about 0.8 to 3 molar equivalents relative to the starting compound Q—H or a salt thereof. This reaction is conducted in an inert solvent such as carbon disulfide, chloroform, carbon tetrachloride or tetrachloroethane, chlorobenzene. The use of chlorosulfonic acid in chloroform causes good results in many cases. The reaction temperature is about 0° to 200° C., preferably about 20° to 120° C. The reaction time is about 20 minutes to several days. In halogenating the compound Q—SO$_3$H or a salt thereof use is made of a halogenating agent, for example a chlorinating agent such as thionyl chloride or phosphorus oxychloride, or a brominating agent such as thionyl bromide or phosphorus oxybromide. The halogenating agent is used in a proportion of about 0.8 to 10 molar equivalents relative to the compound Q—SO$_3$H. In the case that the reaction is conducted in the presence of pyridine, triethylamine, tri-n-propylamine or N,N-dimethylaniline the objective compound is obtained in an improved yield. The reaction temperature is about 20° to 120° C. The reaction time is about 30 minutes to 20 hours.

Process (2)

In the diazotization reaction of compound Q—NH$_2$ or a salt thereof, the starting compound is reacted with sodium nitrite under the usual diazotization conditions, for example in hydrochloric acid under cooling at about −20° C. to 10° C. to give the diazonium salt of the formula Q—N$_2^+$Hal$^-$.

Then, the diazonium salt is reacted with sulfur dioxide in the presence of a copper halide, such as cuprous chloride or cupric chloride to give the compound (VI) or a salt thereof.

The copper halide is used in a proportion of about 0.01 to 3 molar equivalents relative to the diazonium salt. Sulfur dioxide is used in a proportion of about 0.8 to 3 molar equivalent relative to the diazonium salt, and it may be used in large excess. This reaction is conducted under acid conditions. The reaction temperature is about −20° C. to 100° C. The reaction time is about 30 minutes to 12 hours.

Process (3)

In this process, a compound of the formula Q—SR$_{10}$ which is substituted by a divalent sulfur-containing group or a salt thereof is subjected to oxidative halogenation (e.g. chlorination) in the presence of water to give the compound (VI) or a salt thereof. As the halogenating agent use may be made of a chlorinating agent, such as chlorine, sodium hypochlorite, potassium hypochlorite or N-chlorosuccinimide, or bromine. The halogenating agent is used in a proportion of about 1 to 10 molar equivalents relative to the starting compound of the formula Q—SR$_{10}$ or salt thereof. This reaction is preferably conducted under acid conditions, for example by adding hydrochloric acid or acetic acid. The reaction temperature is about −10° C. to 30° C. The reaction time is about 30 minutes to 5 hours.

Process (4)

In this process, hydrogen on the heterocyclic ring e.g. hydrogen on the imidazole ring in the compound of the formula Q—H or a salt thereof is substituted by lithium and the resultant product is reacted with sulfur dioxide to give the lithium sulfinate compound of the formula Q—SO$_2$Li, which is then reacted with a halogenating agent, e.g. a chlorinating agent, to give the compound (VI) or a salt thereof. As the lithiating agent used for the preparation of compound of the formula Q—SO$_2$Li or a salt thereof, use may be made of an alkyllithium such as methyllithium, n-butyllithium or t-butyllithium, lithium amide and lithium diisoprylamide. The lithiating agent is used in a proportion of about 1 to 3 molar equivalents relative to the starting compound Q—H or salt thereof. The sulfur dioxide is used in a proportion of about 1 to 5 molar equivalents. The reaction temperature is about −70° C. to 50° C. The reaction temperature is about 1 to 20 hours.

The halogenating agent used for the subsequent halogenation of compound Q—SO$_2$Li or a salt thereof may for example be a chlorinating agent such as chlorine or N-chlorosuccinimide. The resulting compound (VI) or a salt thereof can be reacted with ammonia to give a compound (IV) or a salt thereof. In the reaction of the compound (VI) or a salt thereof with ammonia, ammonia is used usually in a proportion of about 0.8 to 10 molar equivalents relative to the compound (VI) or salt thereof. This reaction is generally conducted in an inert solvent such as water, ether, THF, acetonitrile, alcohol (e.g. methanol or ethanol), dichloromethane or chloroform. The reaction temperature is about −60° C. to 100° C. The reaction time is about 30 minutes to 8 hours.

The compound (IV) or a salt thereof can be produced in accordance with the following reaction scheme.

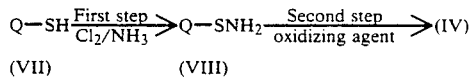

wherein the symbols are as defined hereinbefore.

Examples of the compound of the general formula Q—SH, include, among other compound of the general formula

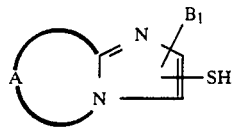

wherein the symbols are as defined hereinbefore.

In the first step, the compound (VII) or a salt thereof is reacted with chlorine or sodium hypochlorite in aqueous ammonia.

This reaction is carried out by the process described in Methoden der Organischen Chemie Vol. 9, p. 277-278.

In the second step, the compound obtained thus (VIII) or salt thereof is oxidized with an oxidizing agent.

As the oxidizing agent, use may be made of hydrogen peroxide, potassium permanganate and metha-chloroperbenzoic acid.

The oxidizing agent may be used in an amount sufficient to make the reaction go to completion; theoretically in an amount yielding 2 equivalents of active oxygen per mole of the starting compound (VIII) or salt thereof.

This reaction is generally conducted in a solvent that does not interfere with the reaction. As the solvents, use may be made of inert solvents such as water, alcohols, e.g. methanol, ethanol, n-propanol, isopropyl alcohol, n-butanol or tert-butanol, aromatic hydrocarbons such as benzene, toluene, xylene, nitrobenzene or chlorobenzene, and halogenated hydrocarbons such as dichloromethane, chloroform, or carbon tetrachloride.

The reaction temperature may be selected from the range of about −60° C. to 100° C. but is preferably in the range of about −20° C. to 50° C. in many cases. The reaction time is comparatively short, generally about 5 minutes to 2 hours.

The compound (IV) can also be produced by the following processes.

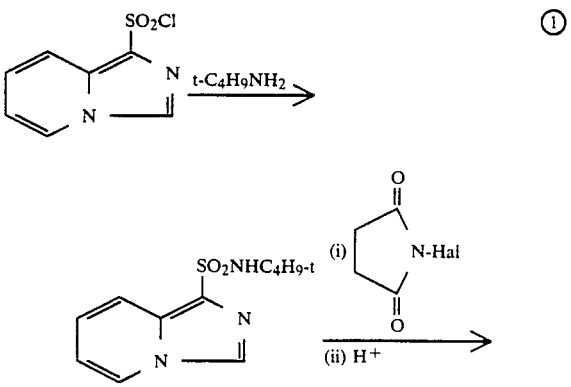

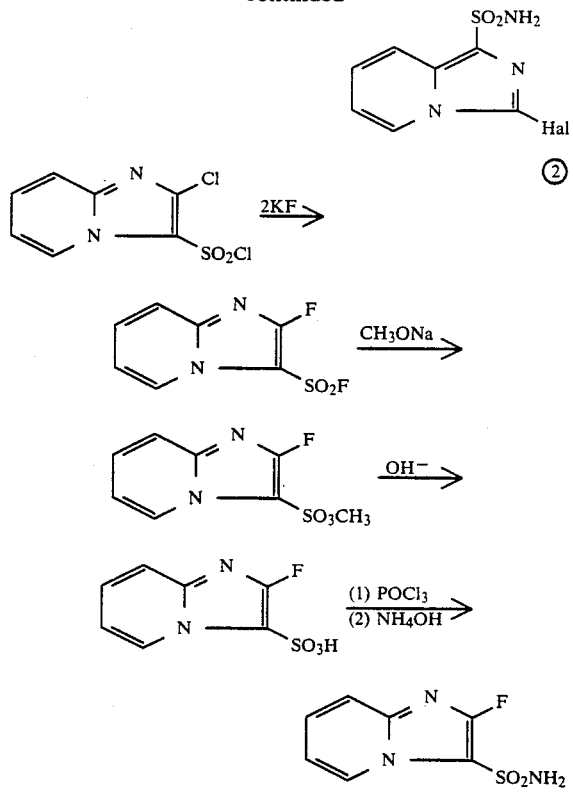
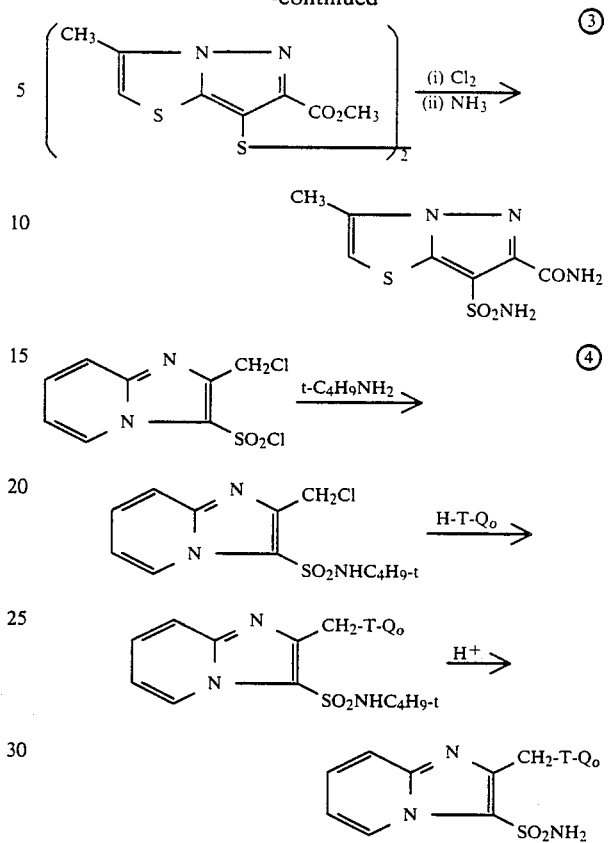
In addition, the substituents on compound (IV) can be easily replaced with different kinds of substituents.
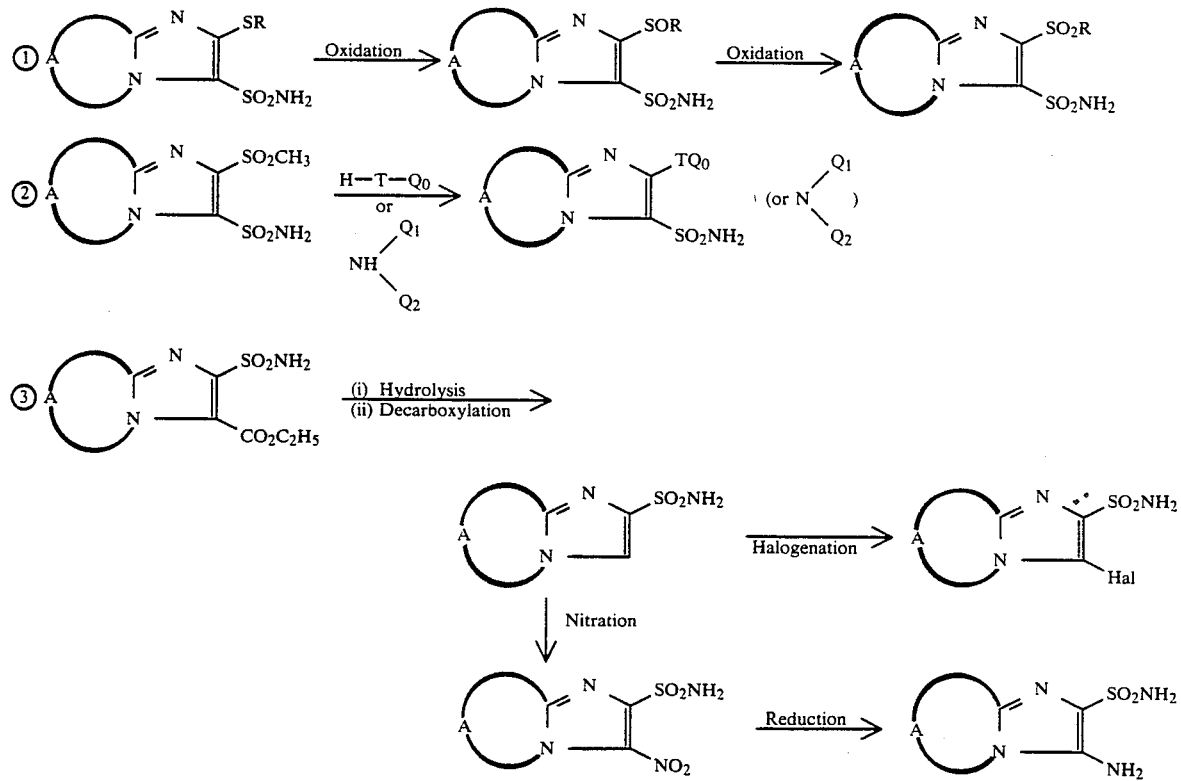

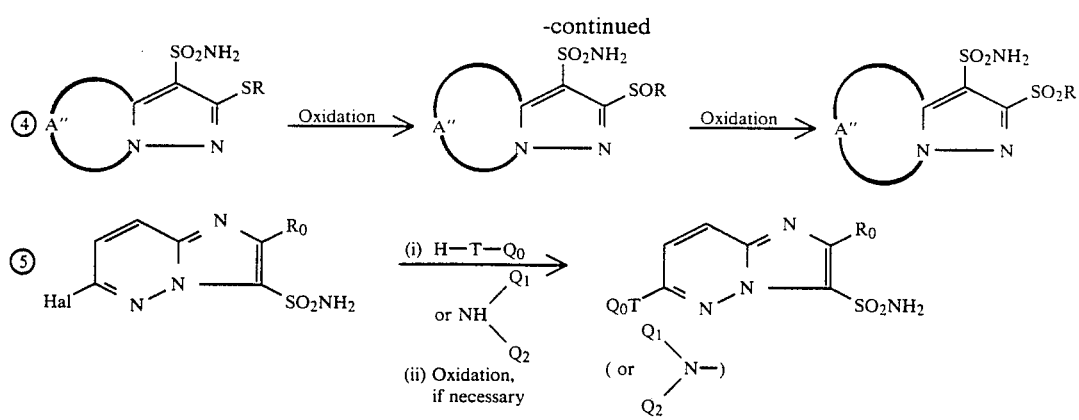

The starting compounds Q—H, Q—NH$_2$ and Q—SR$_{10}$ and their salts can be prepared by the processes described in The Chemistry of Heterocyclic Compounds (Interscience Publisher) 15, Part 1 and Part 2; ibid., 30; Comprehensive Heterocyclic Chemistry (Pergamon Press) 4, and 5; Liebigs Annalen der Chemie 663, 113–117, (1963); ibid., 647, 138 (1961); Journal of Organic Chemistry 49, 3534 (1984); ibid., 38, 1955 (1973); ibid., 36, 11, (1971); ibid., 30, 4081 (1965); ibid., 30, 2403 (1965); Journal of Heterocyclic Chemistry 2, 53 (1965); ibid., 5, 695 (1968); Journal of Medicinal Chemistry 12, 1031, (1969); ibid., 15, 415 and 982 (1972); ibid., 20, 387 (1977); ibid., 21, 235 (1978); Journal of the Chemical Society, 1946 1075; ibid., 1955 2834; ibid., 1963 3277; Chemical and Pharmaceutical Bulletin 11, 1564 (1963); ibid., 12, 813 (1964); ibid., 22, 482 (1974); Journal of the Pharmaceutical Society of Japan 91, 1154 (1971); ibid., 94, 839 (1974); ibid., 98, 631 (1978); Gazzetta Chimica Italiana 105, 777 (1975); Chemical Abstracts 72, 216696 (1970); ibid., 50, 313 (1956); ibid., 73, 87855 and 120548p (1970); ibid., 88, 22752r (1978); U.S. Pat. No. 3,901,903; Japanese Published Examined Patent Application No. 32793/1969; and Farmaco Edizione Scientifica 36, 994 (1981) or by processes analogous thereto.

The processes of producing some representative species of starting compounds are described below.

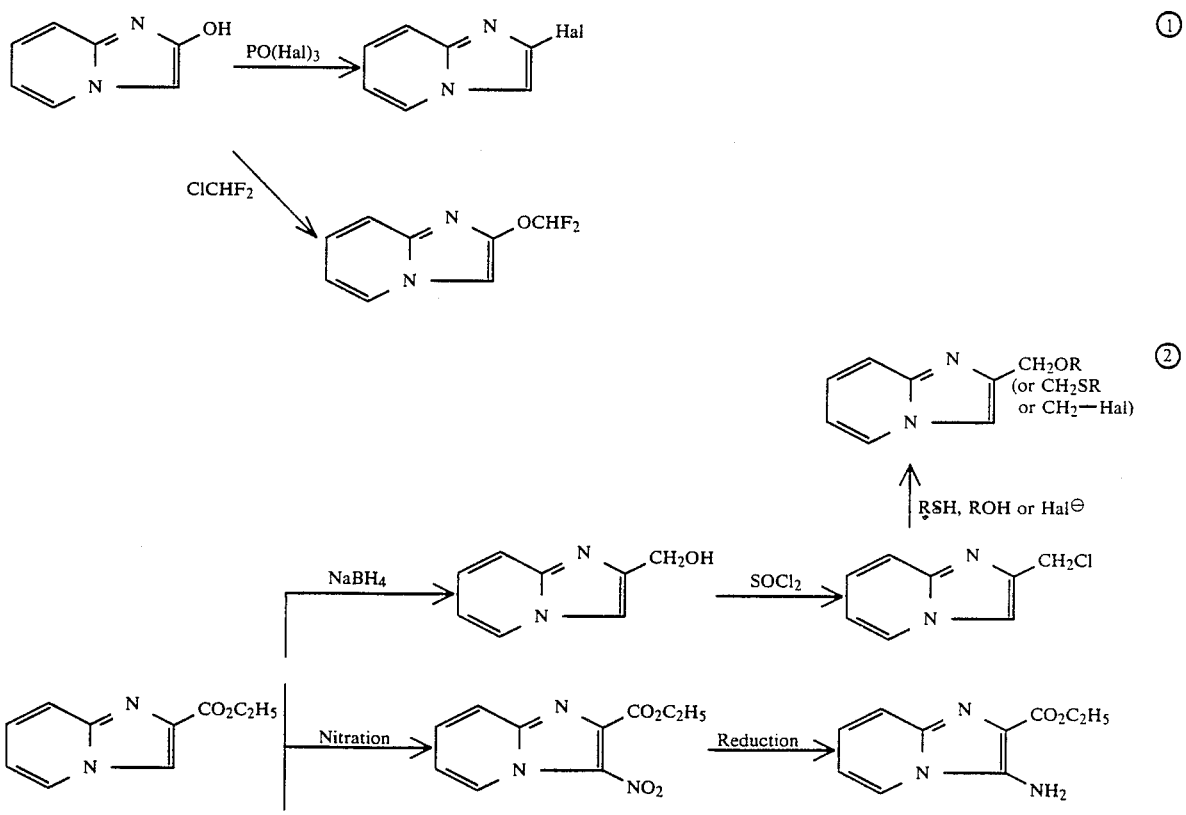

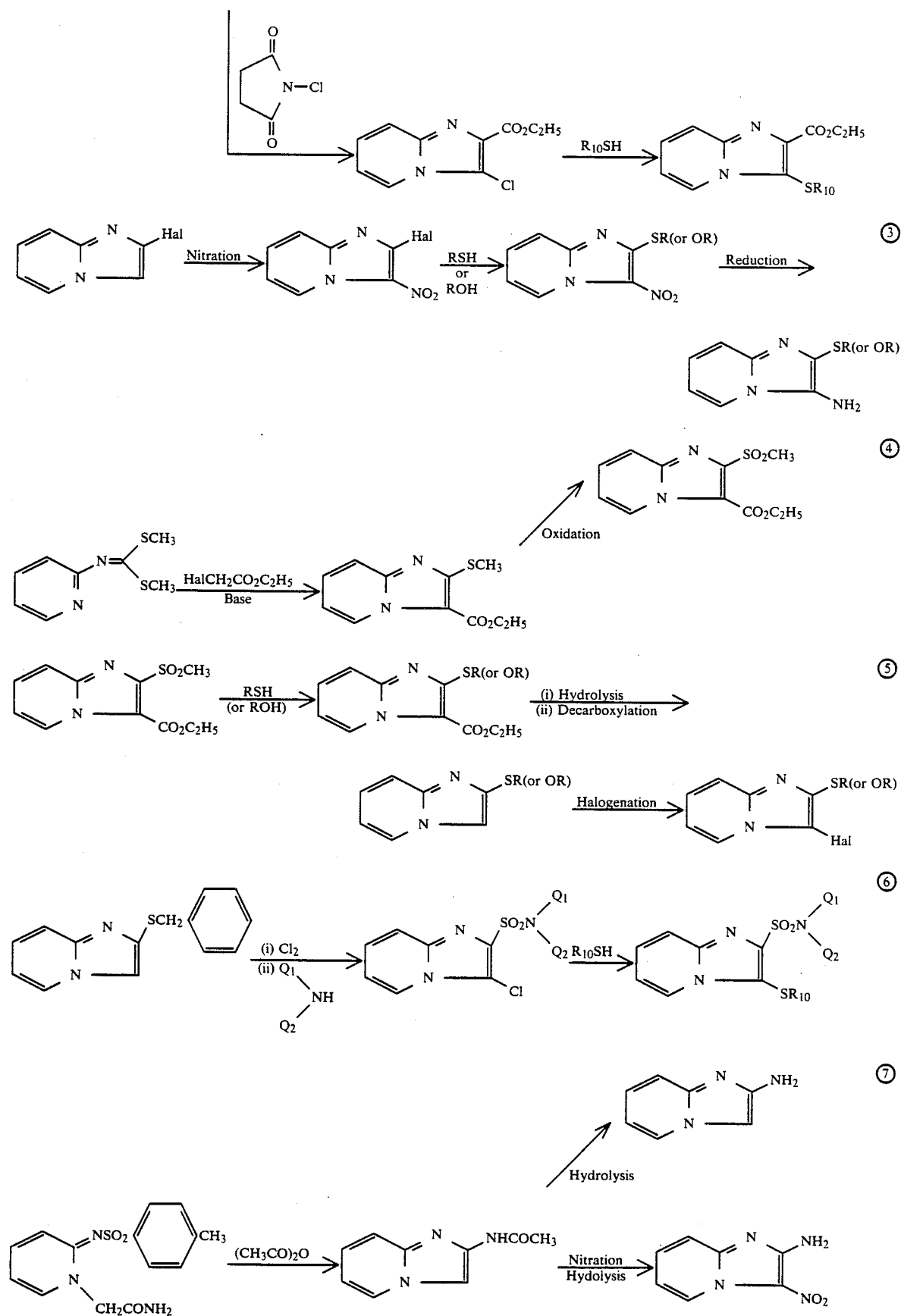

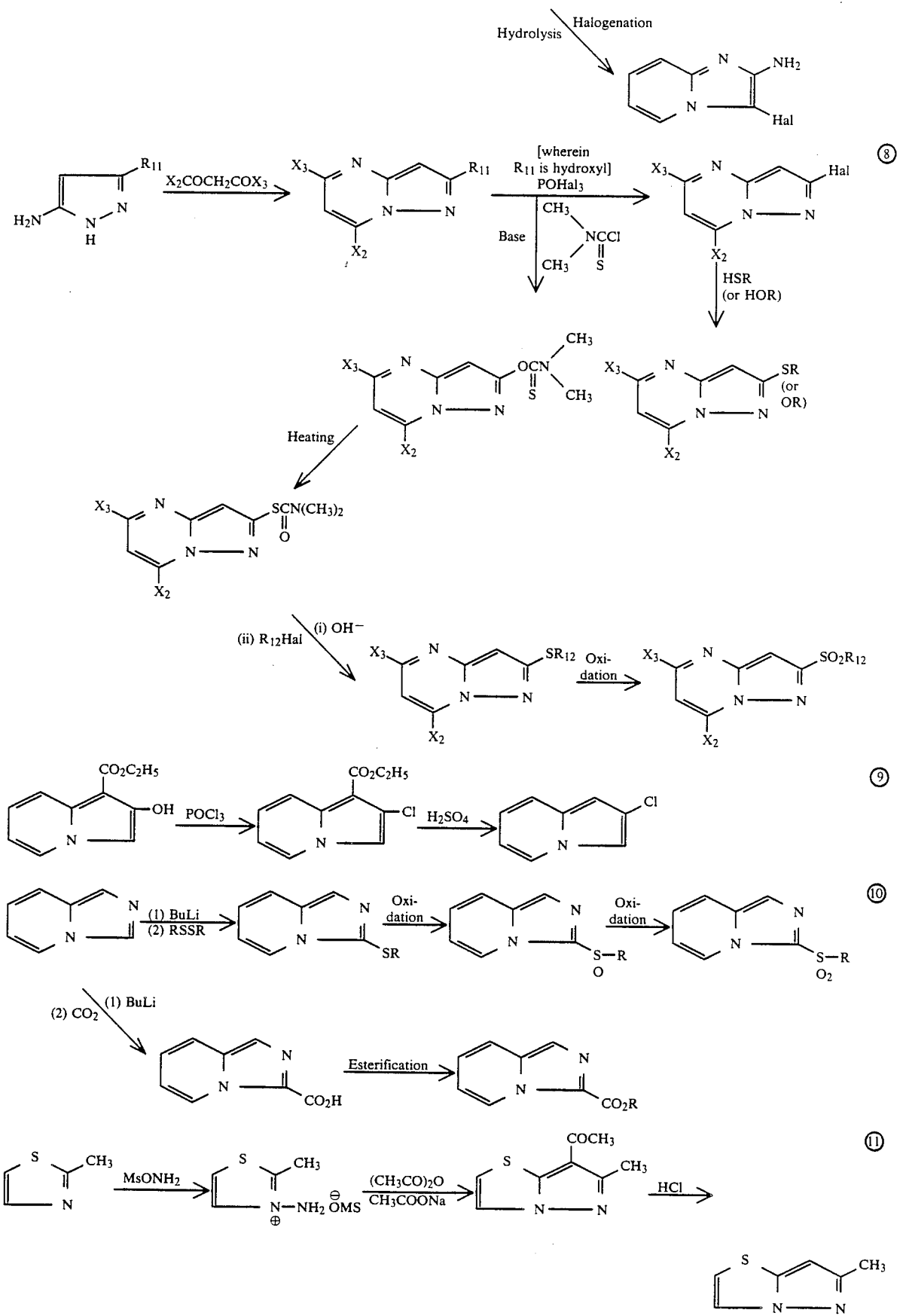

-continued
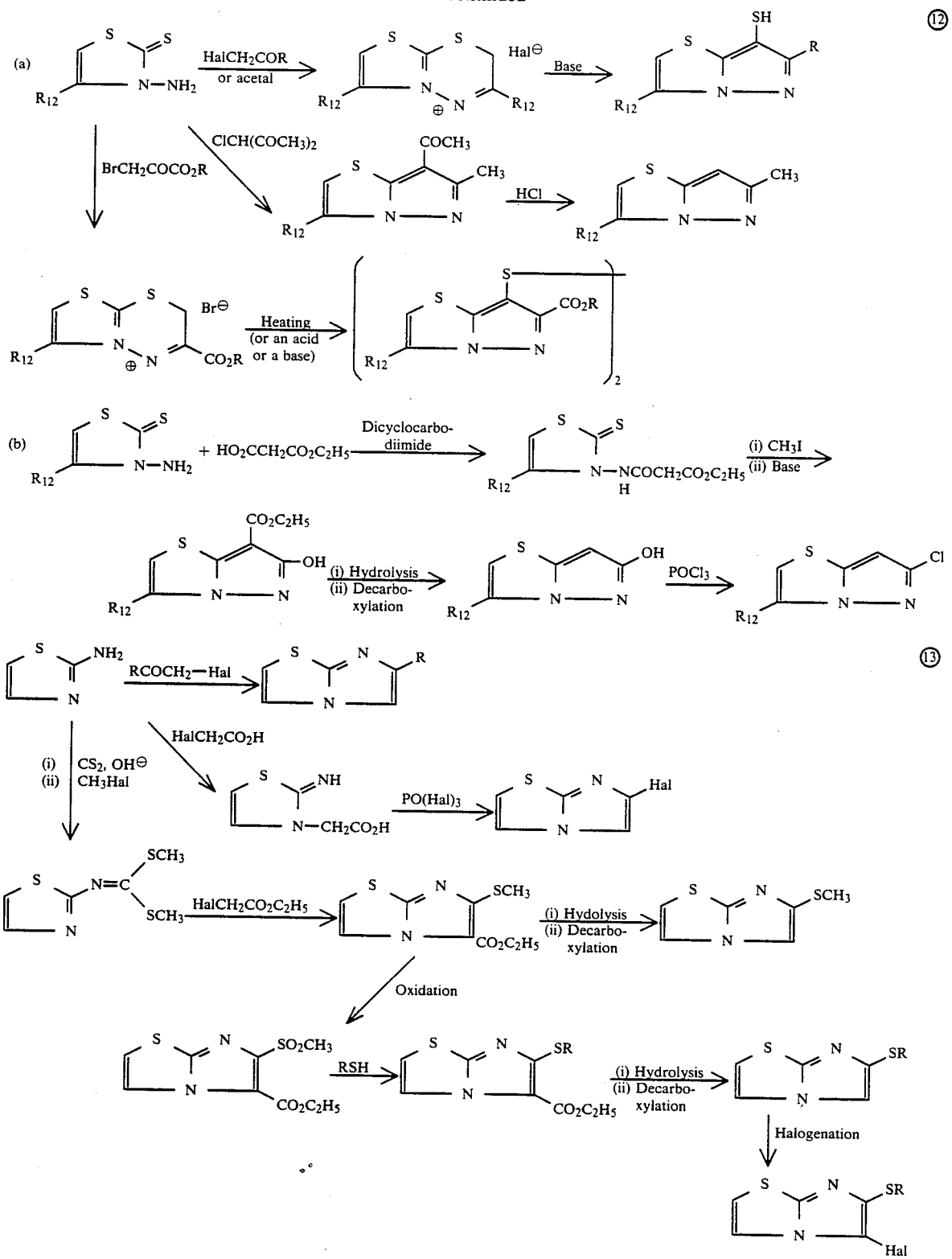
[In the above formulas, $R_{11}$ is an alkyl group containing 1 to 6 carbon atoms such as methyl, ethyl or propyl, hydrogen, or hydroxyl; $R_{12}$ is an alkyl group containing 1 to 6 carbon atoms such as methyl, ethyl or propyl; Ms is

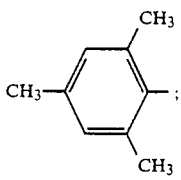

other symbols are as defined hereinbefore]

Among the above reactions, the reaction scheme shown for imidazo[1,2-a]pyridine can be applied to other condensed imidazole compounds such as imidazo[,1,2-a]pyrimidine, imidazo[1,2-a]pyrazine, imidazo[1,2-b]pyridazine, imidazo[1,2-b](1,2,4)triazine, imidazo[1,2-a]imidazole, imidazo[1,2-b]pyrazole, imidazo[2,1-b]thiazole or imidazo[2,1-b](1,3,4)thiadiazole. This method can be applied to other condensed heterocyclic compounds.

By the process of the present invention, the compound (I) or a salt thereof can be easily produced from readily available starting materials in good yield and high purity. The reaction operation is also simple and the reaction process is short. The process of the present invention is very advantageous for industrial production.

The following reference, working and formulation examples are further illustrative of the invention.

The symbols used in the reference and working examples have the following meanings.

S: singlet, d: doublet, t: triplet, q: quartet, d.d: double doublet, m: multiplet, br: broad, J: coupling constant; DMSO: dimethyl sulfoxide.

Unless otherwise indicated, % means % by weight.

The term 'room temperature' generally means a temperature in the range of about 10° to 30° C.

REFERENCE EXAMPLE 1

2-Chloroimidazo[1,2-a]pyridine-3-sulfonic acid

In 20 ml of chloroform is dissolved 3.5 g of 2-chloroimidazo[1,2-a]pyridine, followed by adding dropwise a solution of 4.6 ml of chlorosulfonic acid in 10 ml of chloroform over a period of 20 minutes. The mixture is refluxed with stirring for 6 hours, whereupon a viscous oil is formed. After the supernatant is discarded, ether and a small amount of ethanol are added and the resulting crystals are collected by filtration and dried to give 5.1 g of 1/2 hydrate of the title compound.

NMR (DMSO-$d_6$) δ: 7.21–7.45 (m, 1H), 7.62–7.80 (m, 2H), 8.9 (d, 1H), 9.4 (s, 2H).

REFERENCE EXAMPLE 2

2-Chloroimidazo[1,2-a]pyridine-3-sulfonyl chloride

In 30 ml of phosphorus oxychloride is suspended 5.0 g of 2-chloroimidazo[1,2-a]pyridine-3-sulfonic acid and the suspension is refluxed for 5 hours. After cooling, the reaction mixture is poured in 250 ml of ice-water and extracted with dichloromethane. The dichloromethane layer is separated and dried over anhydrous sodium sulfate and the dichloromethane is distilled off under reduced pressure to give 4.6 g of the title compound as pale yellow crystals.

NMR (CDCl$_3$) δ: 7.2–7.4 (m, 1H), 7.6–7.9 (m, 2H), 8.85 (d, 1H).

REFERENCE EXAMPLE 3

2-Chloroimidazo[1,2-a]pyridine-3-sulfonamide

A solution of 4.6 g of 2-chloroimidazo[1,2-a]pyridine-3-sulfonyl chloride in 60 ml of acetonitrile is added to 60 ml of aqueous ammonia under cooling and the mixture is stirred at room temperature for 2 hours. The acetonitrile is distilled off under reduced pressure and the resulting crystals are collected by filtration and washed with water to give 3.8 g of the title compound. Recrystallization from dilute ethanol gives colorless needles.

m.p 175°–177° C.

NMR (DMSO-$d_6$) δ: 7.2–7.45 (m, 1H), 7.5–7.9 (m, 2H), 8.15 (s, 2H), 8.80 (d, 1H).

The following compounds are prepared by the method described in Japanese Patent Application No. 56250/1987 (corresponding to European Patent Publication No. 0238070).

(1) 6-Methylimidazo[2,1-b]thiazole-5-sulfonamide

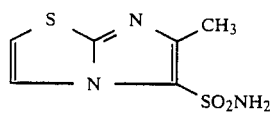

m.p. 192–193° C.

m.p. 192°–193° C.

(2)

2-chloro-6-methoxyimidazo[1,2-b]pyridazine-3-sulfonamide

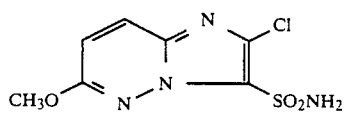

NMR (DMSO-$d_6$) δ: 4.05 (s, 3H), 7.16 (d, 1H), 7.75 (2, 2H), 8.11 (d,1H).

(3)

2-Chloro-6-ethoxyimidazo[1,2-b]pyridazine-3-sulfonamide

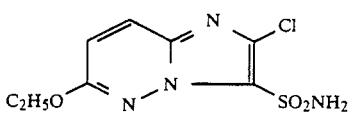

m.p. 225–226° C.

m.p. 225°–226° C.

(4)

2-Chloro-6-(n-propoxy)imidazo[1,2-b]pyridazine-3-sulfonamide

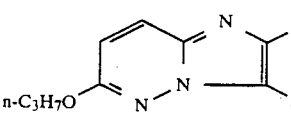

m.p. 198–199° C.

m p. 198°–199° C.

EXAMPLE 1

N-(2-Chloroimidazo[1,2-a]pyridine-3-ylsulfonyl)-N'-(4,6-dimethoxy-2-pyrimidinyl)urea (Compound No. 1)

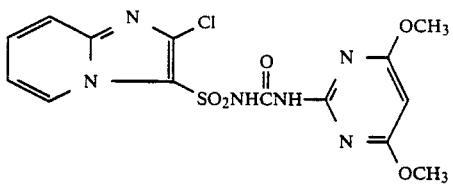

In 30 ml of acetonitrile are dissolved 2.32 g (0.01 mole) of 2-chloroimidazo[1,2-a]pyridine-3-sulfonamide and 2.02 g (0.02 mole) of triethylamine, followed by addition of 1.60 g (0.01 mole) of phenyl chloroformate with stirring at 10° to 20° C. The mixture is further stirred at 20° to 25° C. for 30 minutes, and to the mixture are added 1.00 g (0.010 mole) of methanesulfonic acid and then 1.55 g (0.01 mole) of 2-amino-4,6-dimethoxypyrimidine. The mixture is stirred at 60° C. for 15 minutes. After cooling, the crystals which separates out are collected by filtration and washed with water 3 times with 10 ml of water each. The crystals were then dried in vacuo over $P_2O_5$ to give 3.42 g (yield 83.0%) of the title compound.

m.p. 183°–184° C. (decomp.).

NMR (DMSO-$d_6$) δ: 3.95 (s, 6H), 6.0 (s, 1H), 7.3–7.5 (m, 1H), 7.5–7.9 (m, 2H), 8.97 (d, 1H), 10.65 (s, 1H), 12.8 (s, 1H).

EXAMPLE 2

N-(2-Chloroimidazo[1,2-a]pyridine-3-ylsulfonyl)-N'-(4,6-dimethoxy-2-pyrimidinyl)urea (Compound No. 1)

To 200 ml of dichloromethane are added 10.0 g (0.043 mole) of 2-chloroimidazo[1,2-a]pyridine-3sulfonamide and 8.85 g (0.0866 mole) of triethylamine, followed by adding dropwise 6.78 g (0.0433 mole) of phenyl chloroformate with stirring at 20° to 25° C. The mixture is further stirred at the same temperature for 30 minutes, and 4.20 g (0.0433 mole) of 2-amino-4,6-dimethoxyacid and 6.72 g (0.0433 mole) of 2-amino-4,6-dimethoxypyrimidine are added to the mixture in that order. The mixture is refluxed for 5 hours. After completion of the reaction, the dichloromethane is removed under reduced pressure and to the residue is added 50 ml of acetonitrile. The resulting crystals are collected by filtration, washed with three 10 ml portions of acetonitrile and water with water. The crystals were dried in vacuo over $P_2O_5$ to give 15.62 g (yield 87.9%) of the title compound.

m.p. 183°–184° C. (decomp.).

Table 1 shows the compounds which are prepared by the same procedures as described above.

TABLE 1

| Compound No. | Structural formula | NMR (DMSO$d_6$) | mp (°C.) |
|---|---|---|---|
| 2 | | 2.50(s,3H), 4.05(s,3H), 6.65(s,1H), 7.3~7.5 (m,1H), 7.6~7.9(m,2H), 9.10(d,1H), 10.85(s,1H), 13.0~14.0(br.s,1H) | 166~169 |
| 3 | | 2.50(s,3H), 3.93(s,6H), 5.97(s,1H), 7.47(d,1H), 7.94(d,1H), 10.54(s,1H), 12.75(s,1H) | 180~182 |
| 4 | | 3.84(s,3H), 3.93(s,6H), 6.03(s,1H), 7.29(d,1H), 8.25(d,1H), 10.64(s,1H), 13.10(br.s,1H) | 188~192 |
| 5 | | 1.25(t,3H), 3.93(s,6H), 4.22(q,2H), 6.04(s,1H), 7.24(d,1H), 8.20(d,1H), 10.56(s,1H), 13.00(br.s,1H) | 168~170 |

TABLE 1-continued

| Compound No. | Structural formula | NMR (DMSOd$_6$) | mp (°C.) |
|---|---|---|---|
| 6 | n-C$_3$H$_7$O—[pyridazine]—N=C(Cl)—SO$_2$NHCON(H)—[pyrimidine with OCH$_3$, OCH$_3$] | 0.85(t,3H), 1.4~1.9(m, 2H), 3.94(s,6H), 4.10 (t,2H), 6.00(s,1H), 7.24 (d,1H), 8.20(d,1H), 10.60 (s,1H), 13.10(br.s,1H) | 192~196 |

In addition to the above compounds, the various compounds mentioned in Japanese Patent Application No. 56250/1987 can be produced in good yield by the same procedures as in Examples 1 and 2.

FORMULATION EXAMPLE 1

Emulsifiable concentrate

An emulsifiable concentrate containing:
Compound 1 2 wt. %
Xylene 75 wt. %
Dimethylformamide 18 wt. %
Polyethylene glycol ether (Nonipol 85 ®) 5 wt. %
(To be diluted with water to a suitable concentration before application)

FORMULATION EXAMPLE 2

Wettable powder

A wettable powder obtained by mixing and comminuting the following ingredients.
Compound No. 3 5 wt. %
Sodium ligninsulfonate 5 wt. %
Polyoxyethylene glycol ether (Nonipol 85 ®) 5 wt. %
Clay 80 wt. %
White carbon 5 wt. %
(To be diluted with water to a suitable concentration before application)

FORMULATION EXAMPLE 3

Granules

A granular preparation obtained by mixing the following ingredients with water and granulating the mixture.
Compound No. 2 0.25 wt. %
Sodium ligninsulfonate 2 wt. %
Bentonite 57.75 wt. %
Talc 40 wt. %

FORMULATION EXAMPLE 4

Granules

A granular preparation obtained by mixing the following ingredients with water and granulating the mixture.
Compound No. 1 0.25 wt. %
Sodium ligninsulfonate 5 wt. %
Bentonite 94.75 wt. %

FORMULATION EXAMPLE 5

Granules

A granular preparation obtained by mixing the following ingredients with water and granulating the mixture.
Compound No. 2 0.5 wt. %
Sodium ligninsulfonate 6.0 wt. %
Bentonite 93.5 wt. %

FORMULATION EXAMPLE 6

Granules

A granular preparation obtained by mixing the following ingredients with water and granulating the mixture.
Compound No. 1 0.25 wt. %
Sodium ligninsulfonate 5 wt. %
Bentonite 30.00 wt. %
Clay 64.75 wt. %

TEST EXAMPLE 1 (TEST FOR SELECTIVITY ON RICE)

Paddy soil was put in a square-shaped plastic pot having a surface area of 150 m$^2$. After introducing water and scratching the bed, seeds of Echinochloa Oryzicola, Cyperus difformis, Scirpus juncoides, Lindernia procumberns and Rotala indica were sowed, and further tubers of Sagittavia Pygmaea were planted. Cultivation was effected for a prescribed term, while filling the pot with water up to 3 cm height over the bed surface. On the other hand, paddy soil was put in a Wagner pot having a surface area of 1/10000 are. After introducing water and scratching the bed, 2 nursery rice-plants were transplanted to the bed and the pot was filled with water up to 3 cm height over the bed surface. One week after the transplantation of the rice-plants, when monocotyl weeds grew up to the mono-leaf period, a dilute solution containing the compound (I) was applied into the pot, so that 1 g of the compound (I) was applied per 1 are of the bed surface. The dilute solution was prepared by dissolving 1 g of the compound (I) in 300 ml of acetone containing 2%(w/v) of a surface active agent Tween 20 ® and diluting with water up to 40 l in total.

Three weeks after the application, herbicidal effect against various weeds and harmful effect on the transplanted rice-plant were evaluated according to the following standards:

| Index | Effect | % Inhibition (Herbicidal ration) |
|---|---|---|
| 0 | None | 0 |
| 1 | Slight | 0.1–50 |
| 2 | Weak | 50.1–75 |
| 3 | Moderate | 75.1–87.5 |
| 4 | Strong | 87.6–99.9 |
| 5 | Very strong | 100 |

Harmful effect on rice-plant was shown by the following index numbers (also in the following Test Examples):

| Index | Harmful Effect | % Damage ratio |
|---|---|---|
| 0 | None | 0 |
| 1 | Slight | 0.1–12.5 |

-continued

| Index | Harmful Effect | % Damage ratio |
|---|---|---|
| 2 | Mild | 12.6–25 |
| 3 | Moderate | 25.1–50.0 |
| 4 | Severe | 50.1–99.9 |
| 5 | Very severe | 100 |

The results are shown in Table 2.

| Compound No. | Harmful effect Rice | Herbicidal effect | | | | | |
|---|---|---|---|---|---|---|---|
| | | Echinochloa crus-galli var. oryzicola | Cyperus difformis | Lindernia procumbens | Rotala indica | Scirpus juncoides | Sagittavia pygmaea |
| 1 | 0 | 4 | 5 | 4 | 4 | 4 | 4 |
| 2 | 0 | 4 | 4 | 3 | 4 | 4 | 4 |
| 3 | 0 | 4 | 4 | 3 | 3 | 4 | 4 |
| 4 | 0 | 3 | 4 | 4 | 4 | 4 | 4 |
| 5 | 0 | 4 | 5 | 5 | 4 | 4 | 4 |
| 6 | 0 | 4 | 4 | 3 | 4 | 4 | 4 |

Table II clearly shows that the compound (I) gives no substantial damage to rice and exerts excellent hebricidal effect.

What is claimed is:

1. A process for producing a compound of the formula

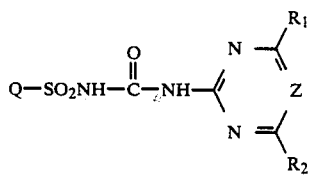

wherein Q is a condensed heterocyclic group which is formed by removing one hydrogen atom bonded to a heterocyclic ring-constituting carbon atom from a condensed heterocyclic ring of the formula

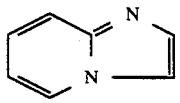

wherein the bonding of Q to $SO_2$ in the compounds always occurs through a heterocyclic ring-constituting carbon atom of Q, which condensed heterocyclic group is unsubstituted or is substituted by one to three of the same or different substituents selected from the group consisting of (1) halogen, (2) straight chain, branched chain or cyclic alkyl having 1 to 6 carbon atoms, which is unsubstituted or is substituted by one to three members selected from the group consisting of (a) straight chain or branched chain alkylthio having 1 to 4 carbon atoms, (b) halogen and (c) straight chain or branched chain alkoxy having 1 to 6 carbon atoms and (3) alkoxy of 1 to 6 carbon atoms, $R_1$ and $R_2$ each are straight chain, branched chain or cyclic alkyl having 1 to 6 carbon atoms or straight chain or branched chain alkoxy having 1 to 6 carbon atoms, and Z is CH, or a salt thereof which comprises the 1st step of reacting a compound of the formula

wherein the symbols are as defined above, with a compound of the formula

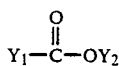

wherein $Y_1$ is halogen, and $Y_2$ is phenyl, in the presence of an alkali metal hydroxide, alkali metal carbonate, alkali metal hydrogen carbonate, alkoxide or organic tertiary amine at a temperature of $-20°$ to $150°$ C. for about 5 minutes to about one hour and the 2nd step of allowing a compound of the formula

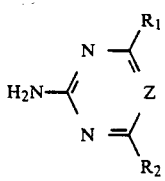

wherein $Z, R_1$ and $R_2$ are as defined above, and an acid selected from an inorganic acid, methanesulfonic acid, ethanesulfonic acid and benzenesulfonic acid to act on the reaction mixture of the 1st step under anhydrous conditions at a temperature of about $10°$ to $100°$ C. for about 10 minutes to about 6 hours.

2. A process as claimed in claim 1, wherein N-(2-chloroimidazo[1,2-a]pyridin-3-ylsulfonyl)-N'-(4,6-dimethoxy-2-pyrimidinyl)urea is produced.

3. A process as claimed in claim 1, wherein the acid in the 2nd step is selected from the group consisting of hydrochloric acid, hydrobromic acid, sulfuric acid, methanesulfonic acid, ethansulfonic acid and benzenesulfonic acid.

* * * * *